(12) United States Patent
Ross et al.

(10) Patent No.: US 9,370,611 B2
(45) Date of Patent: Jun. 21, 2016

(54) TISSUE REMOVAL DEVICES, SYSTEMS AND METHODS

(75) Inventors: Rodney L. Ross, Mission Viejo, CA (US); Gregg Hughes, Mission Viejo, CA (US)

(73) Assignee: Med-Logics, Inc., Laguna Hills, CA (US)

( * ) Notice: Subject to any disclaimer, the term of this patent is extended or adjusted under 35 U.S.C. 154(b) by 19 days.

(21) Appl. No.: 12/683,893

(22) Filed: Jan. 7, 2010

(65) Prior Publication Data
US 2010/0191178 A1    Jul. 29, 2010

Related U.S. Application Data

(60) Provisional application No. 61/143,010, filed on Jan. 7, 2009.

(51) Int. Cl.
*A61M 1/00* (2006.01)
*A61F 9/007* (2006.01)
*A61M 39/24* (2006.01)
*A61B 18/08* (2006.01)

(52) U.S. Cl.
CPC .......... *A61M 1/0037* (2013.01); *A61F 9/00736* (2013.01); *A61M 1/008* (2013.01); *A61M 1/0045* (2014.02); *A61B 18/082* (2013.01); *A61M 2039/2473* (2013.01); *A61M 2039/2486* (2013.01); *A61M 2205/3653* (2013.01); *A61M 2210/0612* (2013.01)

(58) Field of Classification Search
CPC .......... A61M 1/0035; A61M 1/00037; A61M 1/0041; A61M 1/0043; A61M 1/0045; A61M 1/0047; A61M 2039/2473; A61M 2039/2486
USPC .............. 604/22, 35, 118, 119, 121, 131, 133
See application file for complete search history.

(56) References Cited

U.S. PATENT DOCUMENTS

| | | | |
|---|---|---|---|
| 3,595,239 | A | 7/1971 | Petersen |
| 3,597,113 | A | 8/1971 | Dumoulin et al. |
| 3,693,613 | A | 9/1972 | Kelman |
| 3,882,872 | A | 5/1975 | Douvas et al. |

(Continued)

FOREIGN PATENT DOCUMENTS

| | | |
|---|---|---|
| WO | 2005097229 A2 | 10/2005 |
| WO | WO2008157674 A1 * | 12/2008 |
| WO | 2010080894 A2 | 7/2010 |

OTHER PUBLICATIONS

International Search Report and Written Opinion From Corresponding PCT Application No. PCT/US2010/020348, Nov. 4, 2010 (15 pgs).

(Continued)

*Primary Examiner* — Andrew Gilbert
(74) *Attorney, Agent, or Firm* — David P. Gloekler; Olive Law Group, PLLC

(57) ABSTRACT

A tissue removal device includes a cannula that can aspirate tissue, and a thermal element located at a tip of the cannula that can apply localized heat to the tissue to be aspirated. The tissue removal device may also include a device for applying a vacuum in the cannula, which may be configured for applying vacuum pulses according to a controlled pulse rate and vacuum level. The tissue removal device may also include a device for applying the heat at the tip according to a controllable pulse rate and power level.

9 Claims, 17 Drawing Sheets

(56) References Cited

U.S. PATENT DOCUMENTS

| | | | |
|---|---|---|---|
| 4,078,564 A | 3/1978 | Spina et al. | |
| 4,135,516 A | 1/1979 | Spina et al. | |
| 4,191,176 A | 3/1980 | Spina et al. | |
| 4,273,261 A | 6/1981 | Krueger | |
| 4,314,560 A * | 2/1982 | Helfgott et al. | 606/171 |
| 4,597,388 A | 7/1986 | Koziol et al. | |
| 4,674,499 A | 6/1987 | Pao | |
| 4,744,360 A | 5/1988 | Bath | |
| 4,767,403 A * | 8/1988 | Hodge | 604/35 |
| 5,022,413 A | 6/1991 | Spina, Jr. et al. | |
| 5,133,713 A | 7/1992 | Huang et al. | |
| 5,206,255 A | 4/1993 | Ubasawa et al. | |
| 5,217,459 A | 6/1993 | Kamerling | |
| 5,300,069 A | 4/1994 | Hunsberger et al. | |
| 5,312,401 A | 5/1994 | Newton et al. | |
| 5,322,504 A * | 6/1994 | Doherty et al. | 606/167 |
| 5,413,556 A * | 5/1995 | Whittingham | 604/22 |
| 5,423,330 A | 6/1995 | Lee | |
| 5,533,999 A | 7/1996 | Hood et al. | |
| 5,616,120 A | 4/1997 | Andrew et al. | |
| 5,637,112 A | 6/1997 | Moore et al. | |
| 5,651,783 A * | 7/1997 | Reynard | 606/4 |
| 5,674,226 A | 10/1997 | Doherty et al. | |
| 5,697,281 A | 12/1997 | Eggers et al. | |
| 5,817,050 A * | 10/1998 | Klein | 604/35 |
| 5,885,243 A | 3/1999 | Capetan et al. | |
| 6,017,316 A | 1/2000 | Ritchart et al. | |
| 6,112,123 A | 8/2000 | Kelleher et al. | |
| 6,213,997 B1 | 4/2001 | Hood et al. | |
| 6,375,672 B1 | 4/2002 | Aksan et al. | |
| 6,428,508 B1 * | 8/2002 | Ross | 604/118 |
| 6,454,763 B1 * | 9/2002 | Motter et al. | 606/16 |
| 6,468,270 B1 | 10/2002 | Hovda et al. | |
| 6,511,454 B1 | 1/2003 | Nakao et al. | |
| 6,527,766 B1 | 3/2003 | Bair | |
| 6,589,237 B2 | 7/2003 | Woloszko et al. | |
| 6,599,271 B1 * | 7/2003 | Easley | 604/119 |
| 6,648,847 B2 * | 11/2003 | Sussman et al. | 604/27 |
| 6,669,685 B1 | 12/2003 | Rizoiu et al. | |
| 6,731,963 B2 | 5/2004 | Finarov et al. | |
| 7,278,836 B2 | 10/2007 | Hammonds | |
| 8,617,106 B2 * | 12/2013 | Zacharias | 604/119 |
| 2001/0034504 A1 | 10/2001 | Zaleski | |
| 2002/0151835 A1 * | 10/2002 | Ross | 604/22 |
| 2003/0144606 A1 * | 7/2003 | Kadziauskas et al. | 600/565 |
| 2003/0158567 A1 | 8/2003 | Ben-Nun | |
| 2005/0054971 A1 * | 3/2005 | Steen et al. | 604/22 |
| 2005/0234394 A1 | 10/2005 | Ross | |
| 2006/0293646 A1 | 12/2006 | Whayne et al. | |
| 2008/0319374 A1 * | 12/2008 | Zacharias | 604/22 |
| 2010/0010431 A1 * | 1/2010 | Tulley | 604/35 |
| 2010/0094199 A1 * | 4/2010 | Steen et al. | 604/22 |
| 2010/0152762 A1 | 6/2010 | Mark | |
| 2010/0191178 A1 | 7/2010 | Ross et al. | |
| 2010/0280434 A1 | 11/2010 | Raney et al. | |

OTHER PUBLICATIONS

Non-final Office action dated Jan. 21, 2016 from related U.S. Appl. No. 13/602,925.

* cited by examiner

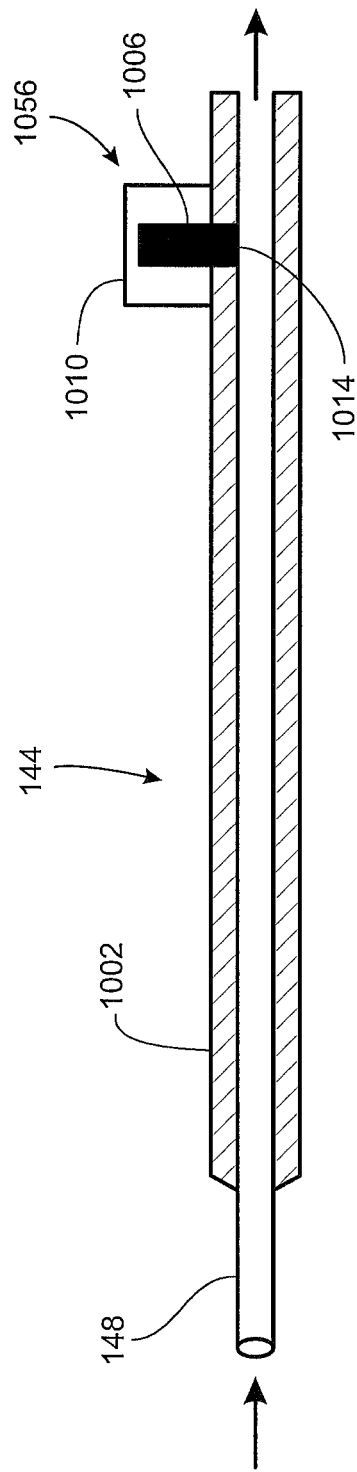
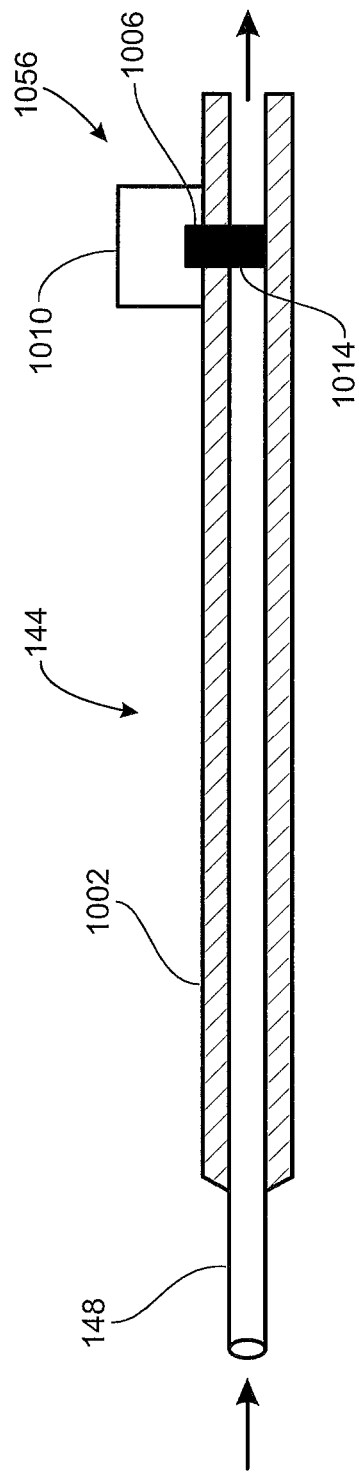

TISSUE REMOVAL DEVICES, SYSTEMS AND METHODS

RELATED APPLICATIONS

This application claims the benefit of U.S. Provisional Patent Application Ser. No. 61/143,010, filed Jan. 7, 2009, titled "TISSUE REMOVAL DEVICES, SYSTEMS AND METHODS;" the content of which is incorporated by reference herein in its entirety.

TECHNICAL FIELD

The present invention relates generally to the removal of tissue, a non-limiting example of which is the removal of cataract material from the eye of a patient. The invention also relates to utilizing vacuum pulses and/or thermal energy to fragment and/or degrade tissue to be removed.

BACKGROUND

Many surgical procedures entail the removal of tissue from the surgical site of operation, including various kinds of ophthalmological procedures. One example of a frequently performed procedure is cataract surgery. The instrument of choice for removing cataracts has been the phacoemulsification ("phaco") device. Phaco technology utilizes ultrasound as the energy modality to fragment and remove the cataract. Specifically, phaco technology uses mechanical ultrasound energy to vibrate a small titanium needle that fragments the cataract material. Aspiration is applied through the titanium needle to remove the cataract material from the eye. A coaxial sleeve supplies irrigation fluid to the eye during the procedure to help neutralize the large amount of heat generated by the vibrating needle.

Phaco technology has many shortcomings. The high ultrasonic energy utilized may result in thermal damage to ocular tissue at the incision site. Moreover, phaco technology is expensive and the phaco procedure is complex and known to have an extended learning curve. Developing nations have been attempting to adopt phaco technology for a number of years, but progress has been slow in many of these countries because of the high cost of the phaco devices and the difficulty surgeons experience in learning the phaco surgical method. There is also a desire on the part of surgeons to make the incision smaller than the current 3.0-mm standard to reduce the surgically induced astigmatism that can be created at the incision site during the phaco procedure. The phaco technique has a tendency to cause a thermal burn at the incision site if the incision is too snug around the phaco tip and its silicone-irrigating sleeve. Regardless of the degree of snugness, the high level of ultrasonic energy employed may cause a thermal burn at the incision or a corneal burn. Also, some of the new foldable intraocular lenses (IOLs) being developed can be inserted into the eye through a 2.5-mm incision. If the surgeon tries to remove the cataract through an incision of this size, there is a higher likelihood that he may experience a thermal effect resulting from the friction created from the ultrasound titanium tip and the silicone irrigation sleeve. This thermal effect can result in tissue shrinkage and cause induced astigmatism.

Moreover, the mechanical ultrasound energy delivered through the titanium tip of the phaco device creates a cavitation field that is intended, along with the mechanical movement of the tip, to fragment the cataract material but it may damage the iris or any ocular tissue or structure it comes in contact with during surgery. The surgeon must be very cautious when activating the ultrasound energy inside the eye. Due to the difficulty in controlling the ultrasound energy, the surgeon often tries to draw the cataract particles to the titanium tip through relatively high fluid flow. Most surgeons try to minimize the movement of the phaco tip in the eye because the high fluid flow and ultrasound energy field reaches well beyond the phaco tip itself. The broad propagation of ultrasonic waves and the cavitation are unavoidable byproducts of the phaco technique; both are potentially harmful and currently are limitations of conventional phacoemulsification.

In addition, ultrasound energy has a tendency to cause corneal edema, especially at higher levels. Many surgeons inject viscoelastic material into the eye prior to inserting the phaco tip into the anterior chamber of the eye to protect the cornea. Some surgeons use viscoelastic material during the stage of the cataract procedure where the IOL is inserted into the eye. Viscoelastic material is expensive and so any reduction in its use would reduce the cost of the cataract procedure.

Moreover, the ultrasound energy created by the phaco device also is known to damage the endothelial cells, located on the inner lining of the cornea. These cells are critical for quality of vision. The harder the cataract, the greater the endothelial cell loss due to the higher level of ultrasound required to emulsify the cataract. It has been reported that in the use of phaco technology, there is an average endothelial cell loss of 13.74% (1.5 to 46.66%) with cataracts that are from a one-plus to a three-plus hardness. It has also been reported that there is an average endothelial cell loss of 26.06% (6.81 to 58.33%) when removing four-plus hardness cataracts with phaco.

The amount of fluid utilized in cataract surgery can have a significant impact on the clarity of the cornea post-operatively and on the overall effectiveness of the surgical procedure. Current phaco devices operate with a partially closed phaco incision due to thermal heat concerns. This incision produces significant amount of fluid outflow from the eye during surgery. To compensate many systems must use higher aspiration flow rates to attract the lens material to the titanium needle. In combination with the higher flow rates, there is a tendency to create higher turbulence and compromise overall ocular chamber stability. It would therefore be more advantageous to be able to operate with a completely closed incision whereby outward fluid flow is directed only through the extraction cannula. With a non-ultrasonic device, such as the device taught in the present disclosure that instead operates on an occlusion principle, fluid use may be minimal and surgical performance enhanced with reduced surgical time.

Moreover, in the future a smaller incision (approximately 1 mm) will be required in order to perform an endocapsular cataract removal to accommodate the injectable IOLs that are being developed by a number of IOL manufacturers. Current phaco technology will not be able to perform an endocapsular procedure due to the limitations in managing heat caused by the mechanical ultrasound.

In view of the foregoing, there is an ongoing need for apparatus and methods for tissue removal that are more cost effective; reduce the risk of damage and cause less damage to surrounding tissues of the surgical site such as a patient's eye, including reducing or eliminating ultrasound thermal energy; reduce the risk of post-operative complications; simplify and reduce the time of the procedure; and reduce the size of the incision site necessary for a given procedure, including accommodating the new Intraocular Lens (IOL) technologies currently under development.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a tissue removal device includes a cannula that can aspirate tissue, and a thermal element located at a tip of the cannula that can apply localized heat to the tissue to be aspirated.

In some implementations, the tissue removal device may also include a device for applying a vacuum in the cannula. In some implementations, the device for applying the vacuum may be configured for applying vacuum pulses according to a controlled pulse rate and vacuum level. In some implementations, the tissue removal device may also include a device for applying the heat at the tip according to a controllable pulse rate and power level.

According to another implementation, a method for removing tissue includes applying localized heat to the tissue from a tip of a cannula, and aspirating the heated tissue through the cannula.

In some implementations, the heat may be applied continuously or in pulses. In some implementations, the tissue may be aspirated by applying vacuum pulses. In some implementations, the vacuum pulses may also be utilized to break up the tissue.

According to another implementation, a tissue denaturing device includes a cannula including an open distal end and an inner passage terminating at the distal end, the inner passage configured to fluidly communicate with a vacuum source; a heat-generating distal element including an annular tip portion constructed from a thermally and electrically conductive material; and a first electrical contact area and a second electrical contact area configured to electrically communicate with an electrical energy source for running electrical current through the annular tip portion, the annular tip portion disposed at the distal end and fluidly communicating with the inner passage, wherein the tissue denaturing device establishes a tissue aspiration path from an environment outside the tissue denaturing device and through the annular tip portion and the inner passage.

According to another implementation, a method for denaturing tissue includes moving a distal section of a tissue denaturing device toward a target tissue to be removed from surrounding tissue, the distal section including a cannula and a heat-generating distal element, the cannula including an open distal end and an inner passage terminating at the distal end, the distal element including an annular tip portion disposed at the distal end and defining a tip opening fluidly communicating with the inner passage; causing the target tissue to move into and occlude the tip opening by generating a vacuum in the inner passage; causing the distal element to generate heat to transfer heat to the target tissue; and utilizing the vacuum generated in the inner passage to aspirate the heated tissue through the tip opening and the inner passage.

According to another implementation, a tissue removal device includes a handpiece enclosing a handpiece interior and having a proximal handpiece opening and a distal handpiece opening; a vacuum conduit extending from the proximal handpiece opening and through the handpiece interior and the distal handpiece opening, and terminating at an open distal conduit end disposed outside the handpiece at a distance from the distal handpiece opening; and a valve mechanism communicating with the vacuum conduit and configured to control vacuum pressure in the vacuum conduit, wherein the vacuum conduit includes a rigid conduit section extending from the valve mechanism to the distal conduit end.

In some implementations, the valve mechanism may include a plunger movable in the vacuum conduit. In some implementations, the plunger may include a sharp edge configured to cut tissue.

In some implementations, the tissue removal device may include a locking element by which the handpiece is removably secured to the vacuum conduit, wherein the locking element is removably secured to the handpiece and is coaxially disposed about the proximal handpiece opening and the vacuum conduit. In some implementations, the tissue removal device may include a hub disposed in the proximal handpiece opening and coaxially interposed between the locking element and the vacuum conduit.

In some implementations, the tissue removal device may include a vacuum transducer configured to measure a vacuum level in the vacuum conduit and vacuum control circuitry communicating with the vacuum transducer, the vacuum control circuitry being configured to switch the valve mechanism between a continuous-vacuum mode, a pulsed vacuum mode, a single-pulse mode, a reduced vacuum-level mode, and a vacuum-off mode in response to a vacuum-level measurement signal received from the vacuum transducer.

In some implementations, the tissue removal device may include two or more vacuum pumps of the same or different type disposed remotely from the handpiece, and a fluid-path switching device communicating with each vacuum pump outlets and with the valve mechanism, wherein the fluid-path switching device is switchable between two or more respective fluid path positions controlling fluid communication between the vacuum pumps and the valve mechanism.

According to another implementation, a method for removing tissue from an eye includes inserting a distal tip of a vacuum conduit of a tissue removal device through an incision formed in the eye and into an interior of the eye; breaking up tissue in the interior by applying a series of vacuum pulses to the tissue via the vacuum conduit, wherein applying the vacuum pulses includes actuating a valve mechanism communicating with a rigid section of the vacuum conduit alternately between an open state and a closed state, the rigid section extending from the valve mechanism to the distal tip; and aspirating the broken-up tissue through the vacuum conduit to a receiving site disposed remotely from the tissue removal device.

In some implementations, wherein the interior is an interior of an anterior capsule of the eye and the tissue includes cataract material.

In some implementations the method includes, prior to breaking up tissue, applying a continuous vacuum pressure in the vacuum conduit, placing the distal tip against an exterior of the anterior capsule while applying the continuous vacuum pressure, creating an entry into the anterior capsule by switching from applying the continuous vacuum pressure to applying a single vacuum pulse, and inserting the distal tip into the anterior capsule. In some implementations, inserting the distal tip into the anterior capsule establishes a peripheral interface between the vacuum conduit and the portion of the anterial capsule defining the entry, and the method includes maintaining a substantially fluid-tight seal between the vacuum conduit and the anterior capsule at the peripheral interface.

In some implementations, the incision has a maximum width of 2.5 mm or less. In some implementations, the maximum width is approximately 1 mm.

In some implementations, the method includes cutting broken-up tissue at a location within the vacuum conduit distant from the distal tip. In some implementations, cutting includes operating a plunger of the valve mechanism.

In some implementations, applying the vacuum pulses includes engaging a foot switch and maintaining engagement with the foot switch, and further including automatically closing the valve mechanism by releasing the foot switch.

According to another implementation, a method for performing eye surgery includes inserting a distal tip of a cannula of a handheld surgical device through an incision formed in the eye and into an anterior capsule of the eye; breaking up cataract material in the anterior capsule by applying a series of vacuum pulses to the cataract material via the cannula, wherein applying the vacuum pulses includes actuating a valve mechanism communicating with a vacuum conduit alternately between an open state and a closed state while the vacuum conduit fluidly communicates with the cannula; aspirating the broken-up tissue through the cannula and the vacuum conduit to a receiving site disposed remotely from the handheld surgical device; moving a selector of the handheld surgical device from a first position at which the cannula communicates with the vacuum conduit to a second position at which the cannula fluidly communicates with a material injection bore; and injecting a material into the anterior capsule via the injection bore and the cannula According to another implementation, a tissue removal device includes a handpiece having a distal handpiece opening; a vacuum conduit disposed in the handpiece; and a cannula extending from the vacuum conduit and terminating at an open distal tip disposed outside the handpiece at a distance from the distal handpiece opening, the cannula including a first cannula wall, a second cannula wall opposite to the first cannula wall, a first seal interposed between the first cannula wall and the second cannula wall, and a second seal interposed between the first cannula wall and the second cannula wall in opposition to the first seal, wherein the first cannula wall and the second cannula wall are constructed from an electrically conductive material, the first seal and the second seal are constructed from an electrically insulative material, and the cannula is attached to the vacuum conduit so as to establish a vacuum-tight fluid path from the distal tip to the vacuum conduit a resistive heating element attached to the first cannula wall and the second cannula wall so as to establish an electrical conduction path from the first cannula wall, through the heating element and to the second cannula wall.

In some implementations, the distal tip of the cannula is coaxially disposed about a longitudinal axis, the resistive heating element includes a loop section coaxially disposed about the longitudinal axis and at least partially circumscribing the longitudinal axis, and the fluid path passes through the loop section and the distal tip to the vacuum conduit. In some implementations, the loop section terminates at a sharp edge.

In some implementations, the resistive heating element includes a wire spanning an inside cross-sectional area of the tapered section. In some implementations, the wire has a cross-hair or S-shaped configuration. In some implementations, the tissue removal device includes a wire retraction device connected to the wire and configured to move the wire between an extended position at which the wire is positioned at the distal tip and a retracted position at which the wire is positioned within the tapered section at a distance from the distal tip.

In some implementations, at least a distal end region of the cannula that includes the distal tip is composed of a resilient material, whereby the opening of the distal tip is conformable to a surface against which the distal tip is placed.

According to another implementation, a method for removing tissue from an eye includes inserting a hollow distal tip of a tissue removal device through an incision formed in the eye and into an interior of the eye; transmitting heat energy to tissue in the eye interior proximate to the distal tip to break up the tissue, by running electrical current through an interior of the handpiece, through a conductive first cannula wall to a resistive heating element located at the distal tip, through the resistive heating element to a conductive second cannula wall, and from the second cannula wall back through the handpiece interior, wherein the first cannula wall and the second cannula wall form a cannula extending from the handpiece and terminating at the distal tip, and wherein most of the heat energy generated by running the electrical current is generated at the resistive heating element; and aspirating the broken-up tissue through the cannula, through a vacuum conduit connected to the cannula and disposed in the handpiece, and to a receiving site disposed remotely from the handpiece, by applying vacuum at the distal tip.

According to another implementation, a method for removing tissue from an eye includes inserting a distal tip of a vacuum conduit of a tissue removal device through an incision formed in the eye and into an interior of the eye; and breaking up tissue in the interior by applying a series of vacuum pulses to the tissue via the vacuum conduit, wherein applying the vacuum pulses includes actuating a valve mechanism communicating with a rigid section of the vacuum conduit alternately between an open state and a closed state, the rigid section extending from the valve mechanism to the distal tip aspirating the broken-up tissue through the vacuum conduit to a receiving site disposed remotely from the tissue removal device.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 10 is a cross-sectional view of an example of a structure of a tissue removal device forming its internal aspiration line, with a vacuum pulsing device in an open position.

FIG. 11 is another cross-sectional view of structure illustrated in FIG. 10, with the vacuum pulsing device in a closed position.

DETAILED DESCRIPTION

Figure 1:
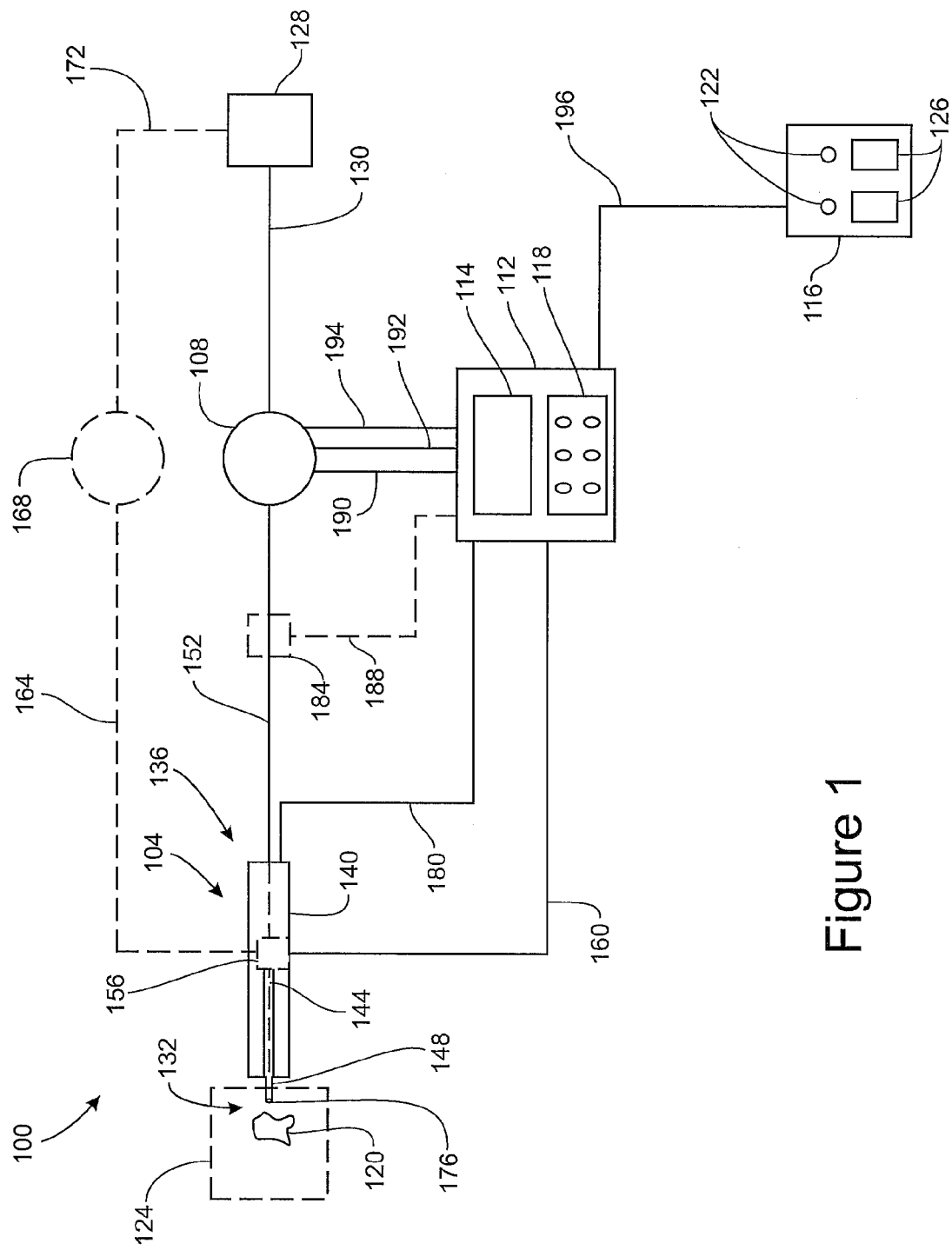
FIG. 1 is a block diagram illustrating an example of a tissue removal system according an implementation disclosed herein.

FIG. 1 is a block diagram illustrating an example of a tissue removal system 100 according an implementation disclosed herein. The tissue removal system 100 generally includes a tissue removal device 104, a vacuum pump 108, and one or more system control devices such as a control console 112 and a foot-operated control device 116. In typical implementations, the tissue removal device 104 is structured and sized to be comfortably handheld by a user, and thus may be referred to as a hand piece, a handheld instrument, or a hand-held device. Other components of the tissue removal system 100 may be stationary or portable and desired or appropriate for a particular procedure for which the tissue removal system 100 is utilized. The tissue removal device 104 and various other components may be provided to a surgeon in a sterile, preassembled Run adapted to be quickly and easily interconnected to complete the tissue removal system 100. The tissue removal device 104 and various other components may be constructed of disposable materials.

Generally, the tissue removal system 100 is adapted for use by a surgeon (or other type of user) to remove target tissue 120 from a surgical site 124 through controlled application of vacuum or both vacuum and thermal energy at a distal tip of the tissue removal device 104. In the present context, target tissue 120 generally encompasses any tissue desired to be removed from the surgical site 124. As an example, the target tissue 120 may be cataract material to be removed from a patient's eye. Vacuum may be utilized not only for aspirating target tissue 120 from the surgical site 124 but also as a modality for breaking up the target tissue 120. Thermal energy may also be utilized for assisting in breaking up the target tissue 120. The tissue removal system 100 may also include a tissue collection site 128 such as may be embodied by any suitable receptacle, container or the like, communicating with the vacuum pump 108 via an outlet line 130, for enabling collection and disposal of aspirated tissue in a sterile manner. Depending on the particular application, the tissue removal system may also be configured to add certain types of materials to the surgical site via the tissue removal device. For example, the tissue removal system may be adapted to apply irrigation fluid to the surgical site, or such function may be performed by a separate instrument. As other examples, the tissue removal device may be configured to inject a material that absorbs cortical material, or a gel or other refractive material that replaces a human lens, a flowable IOL material, etc.

The tissue removal device 104 generally includes an open distal end 132 adapted to be positioned and operated at the surgical site 124, and an opposing proximal end 136. The tissue removal device also includes a housing 140 enclosing various components. As noted above, the housing 140 may be configured (sized, shaped, etc.) to be held in the hand of a surgeon. In advantageous implementations, the housing 140 is constructed of a material that is both electrically and thermally insulating to protect the surgeon, non-limiting examples of which are various thermoplastics and other polymeric compositions. One or more components of the tissue removal device 104 (conduits, tubing, chambers, etc.) provide an internal vacuum (or aspiration) line 144 that runs through the housing 140 generally from the open distal end 132 to or at least toward the proximal end 136. Part of the internal aspiration line 144 is established by a cannula 148 that may extend from a distal opening of the housing 140 over a short distance and terminate at an open distal tip corresponding to the open distal end 132 of the tissue removal device 104. By way of an appropriate fitting (not shown) of the tissue removal device 104 typically located at or near the proximal end 136 (i.e., a proximal opening of the housing 140), the internal aspiration line 144 may be placed in fluid communication with the vacuum pump 108 via connection with an external aspiration line 152 of any suitable length.

The tissue removal device 104 may also include a vacuum pulsing device 156 located within the housing 140 in operative communication with the internal aspiration line 144. With the vacuum pump 108 establishing a controlled level of vacuum, the vacuum pulsing device 156 may be operated to generate vacuum pulses of controlled frequency and duration. For this purpose, the vacuum pulsing device 156 may be placed in electrical communication with the control console 112 via a vacuum pulse control signal line 160. The vacuum pulsing device 156 may be configured in any manner suitable for generating vacuum pulses, some examples of which are described below. To optimize the effect of the vacuum pulsing, the part of the internal aspiration line 144 between the vacuum pulsing device 156 and the open distal end 132 should be rigid so that the as-generated pulsed energy is preserved as it is transferred to the distal end 132. That is, soft conduit materials (e.g., flexible tubing) should be avoided in this part of the internal aspiration line 144 as such materials might provide an undesired damping effect on the pulsed energy. The cannula 148 should thus be constructed from rigid material(s). Depending on the design of the tissue removal device 104, the illustrated cannula 148 may extend from its distal tip to the vacuum pulsing device 156, i.e., over the entire portion of the internal aspiration line 144 that should be rigid. Alternatively, one or more other distinct conduits may be provided between the cannula 148 and the vacuum pulsing device 156, in which case such other conduits should likewise be rigid.

In operation, the vacuum pump 108 provides a base level of vacuum for the tissue removal device 104. This vacuum level may be controlled and adjusted as needed by the surgeon for aspirating tissue. Over any given time period during a tissue removal procedure, the surgeon may set the level of vacuum to be constant or may vary the vacuum level. The vacuum pulsing device 156 may be operated to pulse the vacuum generated by the vacuum pump 108. Vacuum pulsing may be performed for any number of purposes, an example of which is to break up target tissue 120 prior to its aspiration. In one particular example, the pulsed vacuum energy is utilized to break up cataract material. The overall duration of the vacuum pulsing (i.e., the time during which the vacuum pulsing device 156 is active), as well as the pulsing parameters (e.g., the magnitude and duration/frequency of the pulses), may be determined by the surgeon. As examples, the surgeon may be allowed to select among various preset (predetermined, preprogrammed, etc.) vacuum pulsing programs, and/or may be allowed to adjust the vacuum pulsing parameters in real time (on the fly). The surgeon may control the operating parameters of the vacuum pump 108 and the vacuum pulsing device 156 by utilizing the control console 112 and/or the foot control device 116.

Figure 2:
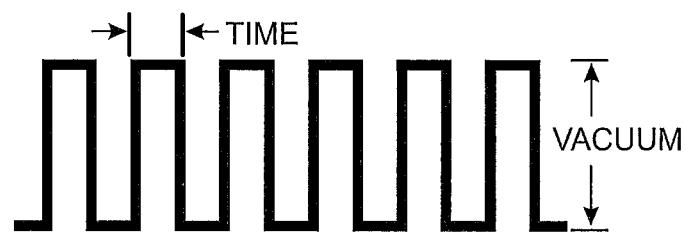
FIG. 2 is an example of a pulsed vacuum signal that may be applied by the tissue removal system.
Figure 3:
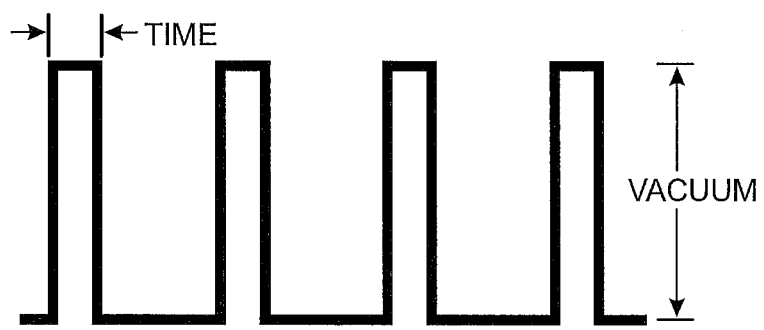
FIG. 3 is another example of a pulsed vacuum signal that may be applied by the tissue removal system.

A few examples of vacuum pulsing programs (or profiles) that may be implemented by the vacuum pulsing device 156 are illustrated in FIGS. 2 and 3. Specifically, FIG. 2 is an example of a pulsed vacuum signal characterized by a relatively high-frequency pulse and moderate vacuum level. FIG. 3 is an example of a pulsed vacuum signal characterized by a relatively low-frequency pulse and high vacuum level. In advantageous implementations, the pulse trains have a stepped profile (i.e., are step functions or square waves) as shown in FIGS. 2 and 3, in which the vacuum level abruptly switches between a high value and a low value (which may correspond to zero vacuum or very low vacuum). That is, the transitions between the high and low values are not ameliorated by ramps or curved functions. By this manner, the pulses in effect constitute a sequence of discrete impacts that are effective for breaking up target tissue 120.

For certain specific purposes of vacuum pulsing, such as the breaking up of certain types of tissue, it may be desirable or necessary for the magnitude of the vacuum pulses to be significantly higher than the magnitude of the base vacuum provided by the vacuum pump 108. Hence, the operation of the vacuum pulsing device 156 may be coordinated with the operation of the vacuum pump 108, which may be done automatically by the control console 112. For instance, the control console 112 may be configured to step up the vacuum level generated by the vacuum pump 108 upon activation of the vacuum pulsing device 156, and likewise to step down the vacuum level upon deactivation of the vacuum pulsing device 156. Moreover, as a safety feature, the control console 112 may be configured to shut down the vacuum pump 108 upon deactivation of the vacuum pulsing device 156, or upon sensing a failure of the vacuum pulsing device 156. This type of coordination is particularly useful for certain types of tissue removal procedures such as cataract removal and other ophthalmological procedures. In such operating environments, the higher vacuum level at which the vacuum pulsing operates could, in the absence of the pulsing, create a potentially harmful high fluid flow-rate condition. That is, when the distal tip of the tissue removal device 104 is located in a fluid environment such as the interior of a patient's eye, the vacuum established by operation of the vacuum pump 108 establishes a fluid flow in the direction from the fluid environment toward the vacuum pump 108, through the cannula 148 and all other fluid conduits comprising the aspiration line.

When the vacuum pulsing device 156 is not being operated, the flow rate primarily depends on the level of vacuum applied by the vacuum pump 108. The tissue removal system 100 is configured to operate the vacuum pump 108 so as to apply vacuum within a range of magnitudes determined to be effective for aspirating target tissue 120 without damaging or otherwise detrimentally affecting nearby tissue or other structures. On the other hand, when the vacuum pulsing device 156 is also active, the vacuum pulses—i.e., the cyclical breaking and restoring of the vacuum applied at the distal tip—significantly affects the fluid flow rate. Generally, the higher the vacuum pulse rate the lower the fluid flow rate, and the lower the vacuum pulse rate the higher the fluid flow rate. Thus, high-frequency vacuum pulses may be applied at a relatively high magnitude to very effectively break up target tissue 120 in a safe manner because the resultant fluid flow rate remains within a safe range. If, however, the vacuum were to remain at that high magnitude after pulsing ceases—due to either deactivation or failure of the vacuum pulsing device 156—then fluid flow rate might quickly increase to an unsafe level. For certain critical surgical sites such as a patient's eye, this sudden jump in fluid flow and/or sudden transition to a continuously applied (non-pulsed) high-magnitude vacuum could cause rapid fluid loss and injury to the patient. Therefore, to eliminate the risk of injury, it is advantageous to coordinate the respective operations of the vacuum pump 108 and the vacuum pulsing device 156.

As just noted, higher vacuum pulse rates result in lower fluid flow rates, and lower vacuum pulse rates result in higher fluid flow rates. Thus, while the tissue removal device 104 is operating in the vacuum-pulse mode the surgeon can control the fluid flow rate, and hence the flow rate of the broken up tissue being aspirated through the tissue removal device 104, by varying the frequency of the vacuum pulses being applied by the vacuum pulsing device 156. The vacuum pulse frequency may be varied by, for example, manipulating an appropriate adjustment knob located on the control console 112 or the foot control device 116. As a safety feature similar to that just described, circuitry provided with the control console 112 or the foot control device 116 may be configured to detect whether a predetermined lower threshold of the vacuum pulse frequency has been reached, and if so respond by automatically lowering the magnitude of the applied vacuum to avoid a dangerously high flow rate. As another safety feature, the foot control device 116 may be configured so as to require a foot switch of the foot control device 116 to remain depressed in order for the vacuum pulsing mode to remain active. By this configuration, if the surgeon intentionally or accidentally removes his foot from the foot switch, the tissue removal system 100 is automatically switched to a continuous vacuum mode with a low vacuum level, or the vacuum pump 108 is automatically shut off, or a valve mechanism of the vacuum pulsing device 156 automatically closes off the aspiration line 144 so as to cut-off application of the vacuum to the distal tip of the cannula 148, etc.

As further shown in FIG. 1, in some implementations the tissue removal system 100 may include a low-vacuum line and a separate high-vacuum line. The above-described first aspiration line 152 is utilized as the low-vacuum line and a second aspiration line 164 is utilized as the high-vacuum line. The first aspiration line 152 and the first vacuum pump 108 are active during the continuous or steady-state vacuum mode in which the surgeon may vary the vacuum level within a range of relatively low vacuum levels. The high-pressure aspiration line 164 interconnects the vacuum pulsing device 156 and a fluid inlet of a second vacuum pump 168 configured for applying relatively higher levels of vacuum associated with the vacuum pulsing mode. Similar to the first vacuum pump 108, the second vacuum pump 168 is controlled by the control console 112 or the foot control device 116 via appropriate electrical signal lines (not shown). The first vacuum pump 108 and the second vacuum pump 168 may be the same type of pump or different types of pumps. The control console 112 or the foot control device 116 is configured to switch between operating the first vacuum pump 108 and the second vacuum pump 168 in accordance with the surgeon's selection of the continuous vacuum mode or the vacuum pulsing mode, or automatically in response to certain events as described elsewhere in the present disclosure. The vacuum pulsing device 156 may be configured to switch the flow path from the cannula 148 into either the first aspiration line 152 or the second aspiration line 164 depending on the mode selected. Thus, fluid and removed tissues flow through either the first aspiration line 152 or the second aspiration line 164. An outlet line 172 may interconnect a fluid outlet of the second vacuum pump 168 and the tissue collection site 128.

The tissue removal device 104 may also include a thermal element 176 located at the distal tip of the cannula 148. The thermal element 176 is adapted to apply localized heat energy to the target tissue 120. The heat energy has the effect of degrading the target tissue 120. In the present context, "degrading" generally means that the target tissue 120 is transformed to a state different from its original state and the different state facilitates the target tissue's removal from the surgical site 124 and/or aspiration through the tissue removal device 104. The precise mechanism of degradation will depend on the nature or composition of the target tissue 120. As a few non-limiting examples, degradation may entail breaking up the target tissue 120 into smaller fractions, denaturing the target tissue 120, depolymerizing the target tissue 120, melting the target tissue 120, etc. In some implementations, the thermal element 176 is an electrically resistive heating element responsive to DC current. The thermal element 176 may be controlled by the control console 112 via a heating signal line 180 that passes a desired magnitude of DC current to the thermal element 176 through one or more electrically conductive components of the tissue removal device 104. As one non-limiting example, the control console 112 may be configured to energize the thermal element 176 over a current range that allows the temperature of the thermal element 176 to be varied within a range of about 40-70° C. The control console 112 may also be configured to transmit pulsed DC current over the heating signal line 180 so as to cause the thermal element 176 to apply pulsed thermal energy. The heating signal line 180 may represent two electrical lines respectively communicating with two terminals or contact points of the thermal element 176, thereby establishing a circuit in which current passes through one electrical line, through the thermal element 176 and through the other electrical line. One or more operating parameters of the thermal element 176 may alternatively or additionally be controlled by the foot control device 116, as described further below.

The thermal element 176 may generally be constructed of any electrically conductive yet electrically resistive material, i.e., a material effective for converting a substantial portion of the electrical energy passing through it to heat energy. Thus, a variety of metals and metal alloys may be utilized. Preferably, the thermal element 176 is composed of a material highly responsive to electrical current, i.e., a highly resistive (or poorly conductive) material, or stated in another way, a material that readily dissipates heat in response to electrical current. One non-limiting example is nichrome. In some implementations, the thermal element 176 may be coated with a material that gives the thermal element 176 a non-stick quality to prevent adhesion or retention of target tissue 120 to the thermal element 176. Non-limiting examples of suitable non-stick coatings include various polymer compositions of the Parylene family as well as chemical derivatives and relatives thereof.

Figure 4:
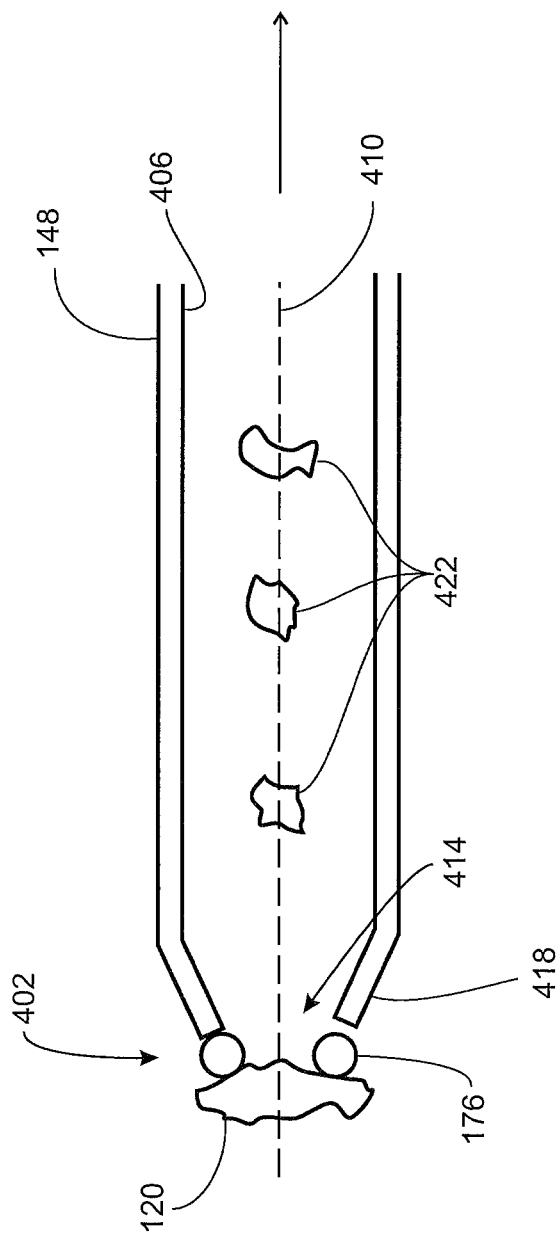
FIG. 4 is a cross-sectional view of an example of a thermal element and a cannula that may be provided by a tissue removal device according to an implementation disclosed herein.
Figure 5:
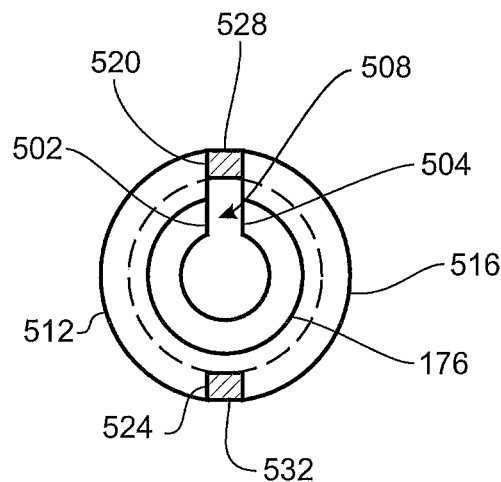
FIG. 5 is an end view of the thermal element and cannula from an outside perspective.

FIG. 4 is a cross-sectional view of an example of a distal region of the tissue removal device 104. More specifically FIG. 4 illustrates, in cross-section, a distal region of the cannula 148 and the thermal element 176 positioned at a distal tip 402 of the cannula 148. An inner surface 406 of the cannula 148 circumscribes the interior of the cannula 148. The inside diameter of the inner surface 406 dictates the cross-sectional flow area through the cannula 148. In this example, the thermal element 176 and the cannula 148 are coaxially arranged about a longitudinal axis 410. An arrow collinear with the longitudinal axis 410 generally depicts the direction of the pressure gradient established by the applied vacuum and thus the direction of fluid flow and tissue aspiration. In this example, the thermal element 176 is provided in the form of a wire loop that defines an opening that serves as a fluid inlet 414 into the cannula 148 and thus corresponds to the open distal end 132 (FIG. 1) of the tissue removal device 104. Accordingly, the thermal element 176 is annular and coaxially surrounds the flow path for aspirated fluid and tissue. The size (internal diameter) of the fluid inlet 414 dictates the flow area into the cannula 176. This is also illustrated in FIG. 5, which is an end view of the thermal element 176 and cannula 148 from an outside perspective. The internal diameter of the thermal element 176 may be the same or substantially the same as the internal diameter of the cannula 148, in which case the flow area is preserved along the axial length of the cannula 148. In other implementations, as illustrated in FIGS. 4 and 5, the internal diameter of the thermal element 176 may be less than the internal diameter of the cannula 148, with the diametrical transition being provided by a tapered (or conical) section 418 of the cannula 148. This configuration may be useful for preventing the cannula 148 from clogging because any tissue small enough to traverse the fluid inlet 414 defined by the smaller-diameter thermal element 176 carries little risk of clogging the larger cross-sectional flow area defined by the cannula 148. As shown in FIG. 5, the thermal element 176 may be C-shaped in that it has two terminal ends 502, 504 separated by a gap 508. By this configuration, respective electrical leads may be attached or otherwise placed in electrical contact with the terminal ends 502, 504 to complete the circuit for passing DC current through the thermal element 176. The electrical leads may in turn communicate with the control console 112 via the heating signal line 180 diagrammatically depicted in FIG. 1.

The tissue removal device 104 may be utilized in a variety of procedures that entail inserting the cannula 148 into a surgical site via an incision. For instance, in various ophthalmological procedures, an incision may be made through a membrane of a patient's eye. The incision may be made by various techniques such as, for example, a laser procedure. To minimize damage to the eye and minimize post-surgery recovery and healing periods, the incision should be as small as possible. Therefore, the cannula 148 should be as small as practicably possible. The design of the cannula 148 and thermal element 176 disclosed herein enables the sizes of these components to be minimized without adversely affecting their functions. In some implementations, the outer diameter of the cannula 148 ranges from about 1.0-3.0 mm. In some examples, the outer diameter of the cannula 148 is about 3.0 mm, 2.5 mm, 2.0 mm, 1.5 mm, or 1.0 mm. As noted elsewhere, the outer diameter of the thermal element 176 may be about the same or less than the outer diameter of the cannula 148. In some examples, the outer diameter of the thermal element 176 is about 1.7 mm or less. The size of the cannula 148 is able to be minimized in part because the tissue removal device 104 itself is not required to provide a means for supplying irrigation fluid to the surgical site. The utilization of the vacuum pulsing effect and the thermal effect disclosed herein does not require nearly as much irrigation fluid as tissue removal techniques of the prior art. Any irrigation fluid needed to be added to the surgical site may be supplied by a separate hand-held device. This may be referred to as a bimanual technique in which the surgeon wields the tissue removal device 104 in one hand and an irrigating device in the other hand as needed. Alternatively, the tissue removal device 104 may be configured for performing a coaxial technique in which irrigation fluid is supplied by the tissue removal device 104 through an annular sleeve (not shown) coaxial with the cannula 148. This latter alternative would require a larger incision, although the incision may still be less than 3.0 mm.

FIG. 4 also illustrates an example of the thermal effect implemented by the thermal element 176. In this example, the target tissue 120 (such as, for example, a cataract or portion of a cataract) has been drawn to the fluid inlet 414 under the influence of the applied vacuum. The target tissue 120, however, is larger than the fluid inlet 414 and hence initially comes into contact with the thermal element 176 and occludes the fluid inlet 414. In some situations, the applied vacuum may be sufficient to deform the target tissue 120 enough to enable the target tissue 120 to traverse through the fluid inlet 414 and flow through the cannula 148, out from the tissue removal device 104, and through associated aspiration lines to a desired destination (e.g., the collection site 128 illustrated in FIG. 1). In other situations, the target tissue 120 may be too large and/or not sufficiently deformable to be aspirated solely under the influence of the applied vacuum, and/or the implementation of the vacuum pulsing effect may not be effective enough to break up the target tissue 120. In these latter situations, the thermal element 176 may be energized to apply heat energy to the target tissue 120 and thereby break up the target tissue 120 into smaller fragments 422 more easily transported through the fluid inlet 414 and cannula 148.

Additionally, the tissue removal system 100 may be configured to detect the occurrence of occlusion and automatically activate the thermal element 176. Various approaches may be taken for detecting the occluding event. As one non-limiting example, the tissue removal system 100 may provide a pressure transducer 184 (FIG. 1), operatively interfaced with the aspiration line 152 at an appropriate location thereof, which provides continuous or intermittent pressure feedback signals to the control console 112 via a pressure feedback signal line 188. The detection of an abrupt change in pressure (or vacuum) level in the aspiration line 152 may be interpreted as the occurrence of an occluding event at the fluid inlet 414 (FIG. 4) and automatically trigger activation of the thermal element 176. Likewise, when the tissue removal system 100 is operating in continuous vacuum mode, the detection of an occluding event may trigger activation of the vacuum pulsing mode. The control console 112 may be configured to decide whether to automatically trigger the vacuum pulsing mode and/or the thermal application mode, and whether to activate both modes simultaneously or sequentially, depending on the current state of operation of the tissue removal device 104 at the time of detection of an occlusion. When it is subsequently detected that the occlusion has been lost, the control console 112 may be configured to deactivate the vacuum pulsing device 156 and/or the thermal element 176, and/or may shut down the vacuum pump(s) 108, 168 or otherwise cause vacuum to be cut off at the distal tip 402. For the purpose of detecting occlusions, the pressure transducer 184 may be positioned in the housing 140 (FIG. 1) of the tissue removal device 104 in operative communication with some portion of the internal aspiration line 144. Alternatively, as shown in FIG. 1 the pressure transducer 184 may be positioned in operative communication with the external aspiration line 152 or 164, or within the housing of the vacuum pump 108 or 168.

It will be noted that the effectiveness of the thermal effect does not in all situations require actual contact between the target tissue 120 and the thermal element 176. For instance, upon inserting the distal tip 402 of the cannula 148 into a surgical site, the thermal element 176 may be located at a small distance from the target tissue 120. The thermal element 176 may then be activated while it is in proximity to, but not contacting, the target tissue 120. Heat energy from the thermal element 176 may be transferred to the target tissue 120 through a small portion of the fluid medium existing between the thermal element 176 and the target tissue 120 such as air or fluid (e.g., intraocular fluid in the case of an ophthalmologic procedure, and/or irrigation fluid as may be applied in a variety of surgical procedures). A sufficient amount of heat energy may be transferred through the fluid medium to cause the target tissue 120 to begin to break up prior to the target tissue 120 being drawn to the fluid inlet 414 surrounded by of the thermal element 176. Alternatively or additionally, the target tissue 120 may begin to break up while in transit toward the fluid inlet 414 due to the transfer of heat from the thermal element 176.

In all such situations, it is evident that the thermal effect is highly localized. The thermal element 176 is shaped so as to present an outer surface area that concentrates the emitted heat energy directly into the fluid inlet 414 and the immediate vicinity of the fluid inlet 414. The thermal effect is effective and rapid enough that no substantial portion of fluid volume in which the target tissue 120 resides needs to become heated to any appreciable degree. The thermal effect is also effective and rapid enough that the heat energy need only be applied for a very brief period of time. This period of time is insufficient for surrounding non-targeted tissue to be adversely affected by the applied heat energy. This is particularly so in procedures entailing the circulation of irrigation fluid through the surgical site as the irrigation fluid absorbs excess heat energy deposited by the thermal element 176. The period of time for heat activation may also be minimized by applying pulses of heat energy as noted above, in procedures where a pulsed thermal effect is found to be more effective than a constant application of heat. Moreover, the thermal element 176 is positioned, sized and shaped such that the surgical site is exposed to a minimal surface area of the thermal element 176. As an example, the distance over which the thermal element 176 extends axially outward from the distal tip 402 of the cannula 148 may be about 2 mm or less. In other implementations, the thermal element 176 may be positioned so as to be partially or fully recessed within the distal tip 418 of the cannula 148.

Figure 6:
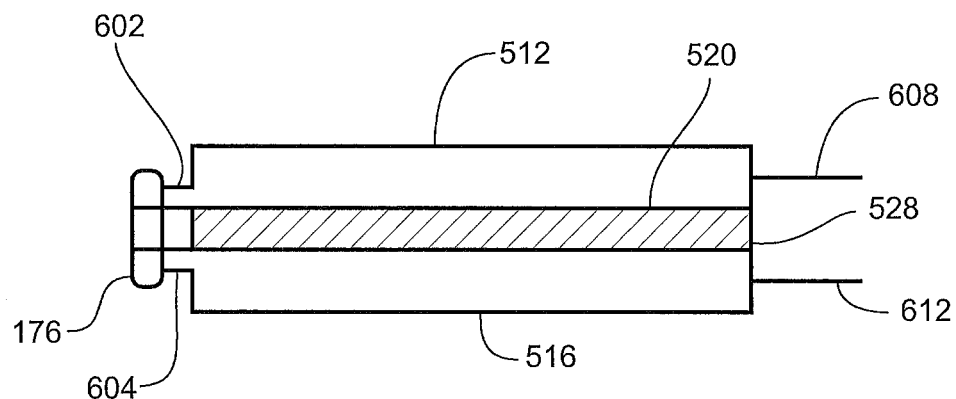
FIG. 6 is a top view of the thermal element and cannula illustrated in FIGS. 4 and 5.

FIGS. 4 and 5 additionally illustrate an implementation in which the structure of the cannula 148 itself is utilized to conduct DC current to the thermal element 176. This implementation is also illustrated in FIG. 6, which is a top view of the thermal element 176 and cannula 148 illustrated in FIGS. 4 and 5. In this case, the cannula 148 has a split-structured design in which the cannula 148 includes two C-shaped or semicircular, electrically conductive structural members 512, 516 extending along the longitudinal axis 410. The structural members 512, 516 may be composed of any suitable conductive material. In advantageous implementations, the structural members 512, 516 are composed of a material that is a very good conductor, i.e., conducts electricity very efficiently and thus without generating undue amounts of resistive heat. In this manner, the thermal effect imparted by the thermal element 176 remains localized at the distal tip 402 of the cannula 148 and very little heat is emitted by the cannula 148. This is particularly useful for avoiding thermal damage to membranes or other tissues through which an incision has been made and which may therefore be in direct contact with the outer perimeter of the cannula 148 extending through the incision. Non-limiting examples of materials suitable for the cannula members 512, 516 include aluminum, copper, nickel, and various precious metals (e.g., gold, silver, platinum, etc.).

From the perspective of FIG. 5, the structural members 512, 516 of the cannula 148 are separated from each other by an upper gap 520 and a diametrically opposing lower gap 524. As shown in FIG. 6, the gaps 520, 524 are axially elongated and continue along the entire axial distance of the cannula 148. By this configuration, the two members 512, 516 are electrically isolated from each other and hence may be utilized as electrical conduits for passing DC current to the thermal element 176. For this purpose, the two members 512, 516 may include respective extensions 602, 604 (or projections, tabs, or the like) in electrical contact with the terminal ends 502, 504 of the thermal element 176. All other conductive portions of the cannula 148 are physically separated from the thermal element 176. As diagrammatically depicted in FIG. 6, the two members 512, 516 may respectively communicate with two other electrical conductors 608, 612 that may be provided in the tissue removal device 104, which in turn may communicate with or form a part of the heating signal line 180 shown in FIG. 1.

To fully enclose the fluid volume circumscribed by the cannula 148 and seal this part of the aspiration line, axially elongated seals 528, 532 may be positioned so as to respectively fill the gaps 520, 524 between the cannula members 512, 516. The axial seals 528, 532 may be composed of any suitable electrically insulating material. In other implementations, the seals 528, 532 may be radial projections extending from a structure of the tissue removal device 104 external to the cannula 148, such as a cylinder that partially or fully surrounds the two members 512, 516 of the cannula 148. The seals 528, 532 may also extend from or be supported by an internal portion of the housing 140 of the tissue removal device 104.

Figure 7:
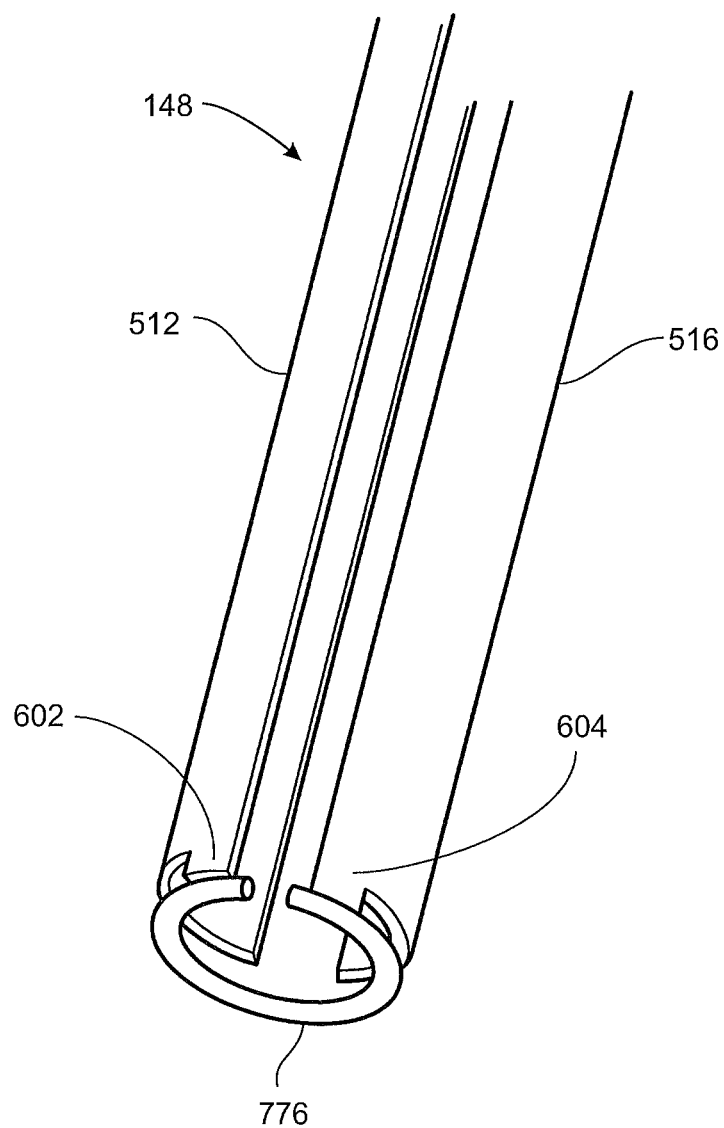
FIGS. 7, 8 and 9 are perspective views of the cannula and respective examples of how the thermal element may be structured.
Figure 8:
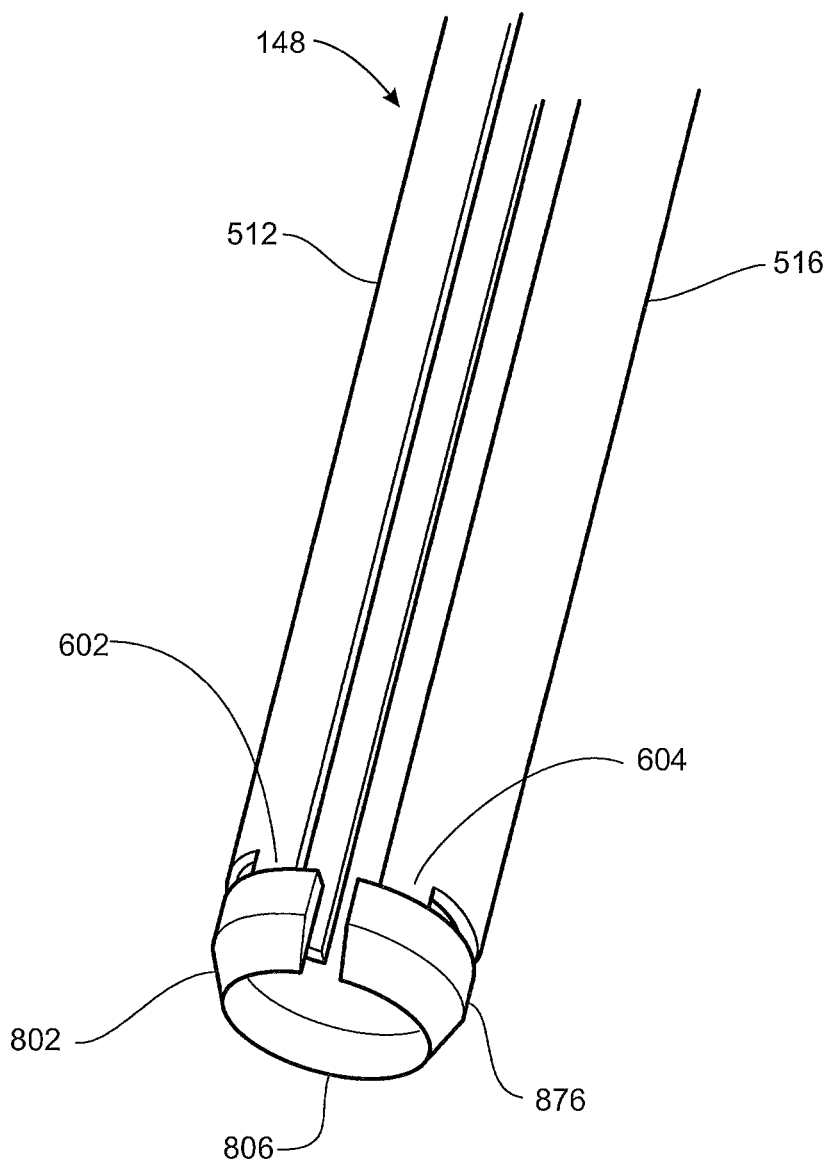
Figure 9:
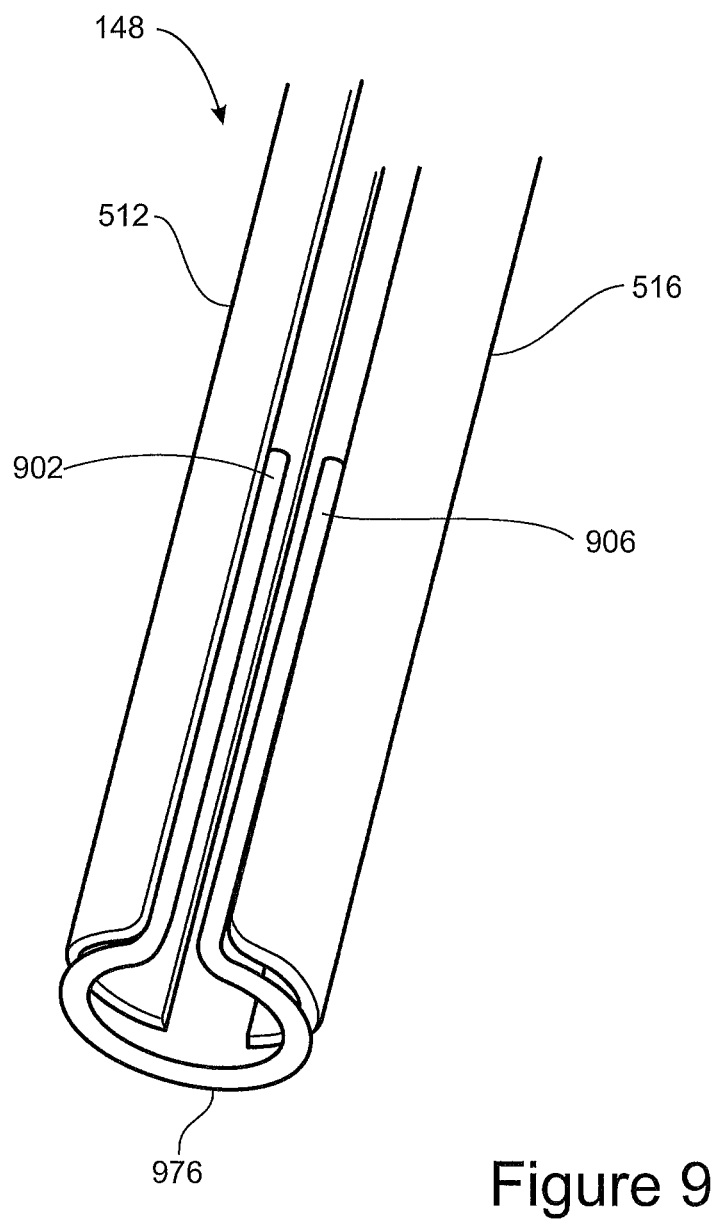

FIGS. 7, 8 and 9 are perspective views of the distal portion of the cannula 148 and respective examples of how the thermal element may be structured. In each of these examples, the cannula 148 has the above-described split design with two curved members 512, 516 electrically isolated from each other. For ease of illustration, seals interposed between the members 512, 516 are not shown. Also, in these examples, the cannula 148 has a constant diameter. FIG. 7 illustrates a thermal element 776 that is ring-shaped with a gap 508, similar to that described above and illustrated in FIGS. 4, 5 and 6. FIG. 8 illustrates a thermal element 876 that is also ring-shaped with a gap 508. In comparison to FIG. 7, the thermal element 876 of FIG. 8 has a larger axial dimension. This facilitates shaping the thermal element 876 for specific purposes. For instance, as shown in FIG. 8, a distal-most portion 802 of the thermal element 876 may taper down to a sharp edge 806, which may assist in breaking up large target tissue drawn into contact with the thermal element 876 and/or provide an even more localized thermal effect at the sharp edge 806. In addition, the inside diameter of distal-most portion 802 may taper down from the inside diameter of the cannula 148 to prevent clogging in a manner similar to the tapered section 418 of the cannula 148 illustrated in FIGS. 4, 5 and 6. FIG. 9 illustrates a thermal element 976 that includes two axial legs 902, 906 extending in the axial direction along at least a portion of the length of the cannula 148. The axial legs 902, 906 may, for example, be positioned in one of the gaps between the split members 512, 516 of the cannula 148. The axial legs 902, 906 may be provided to extend the thermal effect over a desired length of the distal region of the cannula 148.

The positions of the thermal elements 776, 876, 976 may be fixed relative to their respective cannulas 148 in any suitable manner. For example, in FIG. 7 the terminal ends of the thermal element 776 may be placed in electrical communication with the respective cannula extensions 602, 604 by welding, soldering, or an electrically conductive adhesive. In FIG. 8, the thermal element 876 may be attached to its cannula 148 in a similar manner. In FIG. 9, the axial legs 902, 906 (serving as terminal ends) of the thermal element 976 may be attached to respective inside edges of its cannula 148 in a similar manner. Alternatively in FIG. 9, the axial legs 902, 906 may be attached to respective insulated wires (not shown) that run along the cannula 148 and in communication with the heater signal line 180 (FIG. 1). In this latter case, the structural members 512, 516 of the cannula 148 are composed of an electrically insulating material instead of a conductive material.

While the various cannulas 148 described thus far are oriented along a straight axis, this is not a limitation of the present teachings. In some implementations, the cannula 148 provided with the tissue removal device 104 may be curved or angled. In other implementations, the radius of curvature or the angle of the cannula 148 may be adjustable. That is, the surgeon may elect to utilize a straight-shaped cannula 148 or be able to bend the cannula 148 to conform to a desired curved or angled shape. This adjustability of the cannula 148 may be implemented in a variety of ways, such as by selecting a material that is malleable (yet still rigid so as not to dampen vacuum pulses), providing the cannula 148 in the form of a series of segments that are movable relative to each other, etc. An adjustable cannula 148 may be useful in certain surgical sites that are difficult to access, do not have straight boundaries, or have unpredictable boundaries. A few examples include blood vessels, various biological ducts, and various anatomical cavities.

FIGS. 10 and 11 are cross-sectional views of an example of a structure of the tissue removal device 104 forming its internal aspiration line 144. FIG. 10 shows the aspiration line 144 in an open position, while FIG. 11 shows the aspiration line 144 in a closed position. The structure includes the cannula 148, another suitable fluid conduit such as a tube 1002 in fluid communication with the cannula 148, and a vacuum pulsing device 1056 in operative communication with the aspiration tube 1002. The cannula 148 may be structured according to any of the implementations described herein. As noted above, the cannula 148 and at least that portion of the aspiration tube 1002 between the vacuum pulsing device 1056 and the cannula 148 should be rigid so as to optimize the vacuum pulsing effect. The vacuum pulsing device 1056 may have any design suitable for alternately closing and opening the fluid path through the aspiration tube 1002 and hence alternately breaking and restoring vacuum. For this purpose, in some implementations the vacuum pulsing device 1056 includes a movable member 1006 that may be actuated to alternately extend into and retract from the fluid path. The movable member 1006 may be configured to obstruct all or part of the fluid path when extended therein such that the cycling of the movable member 1006 between its extended and retracted positions generates vacuum pulses. As noted above, the vacuum pulsing effect may be utilized to break up target tissue. The vacuum pulsing effect may be implemented alternatively or in conjunction with the thermal effect. Moreover, the vacuum pulsing effect and the thermal effect may be implemented in sequence or simultaneously. When implemented in sequence, the vacuum pulsing effect may follow the thermal effect, or vice versa. The sequencing of the two effects may be repeated over one or more alternating cycles. Accordingly, in a given tissue removal procedure, a surgeon may elect to activate the vacuum pulsing effect only, or the thermal effect only, or both effects according to a desired sequence, or both effects simultaneously to achieve a synergistic effect.

In the example specifically illustrated in FIGS. 10 and 11, the vacuum pulsing device 1056 is a solenoid-based device that includes a solenoid actuator 1010. The movable member 1006 serves as the plunger that is translated by the actuator 1010. The movable member 1006 translates through an opening 1014 in the aspiration tube 1002. A seal of any suitable design may be provided at the physical interface between the movable member 1006 and the tube opening 1014 as needed to maintain the aspiration tube 1002 in a fluid-tight condition. As one non-limiting example, the seal may be an elastic material that covers the tube opening 1014. As the movable member 1006 translates into the aspiration tube 1002 through the tube opening 1014, the seal stretches and deforms around the movable member 1006, thereby covering the movable member 1006 as well as the tube opening 1014 and maintaining fluid isolation between the interior and exterior of the aspiration tube 1002.

Figure 12:
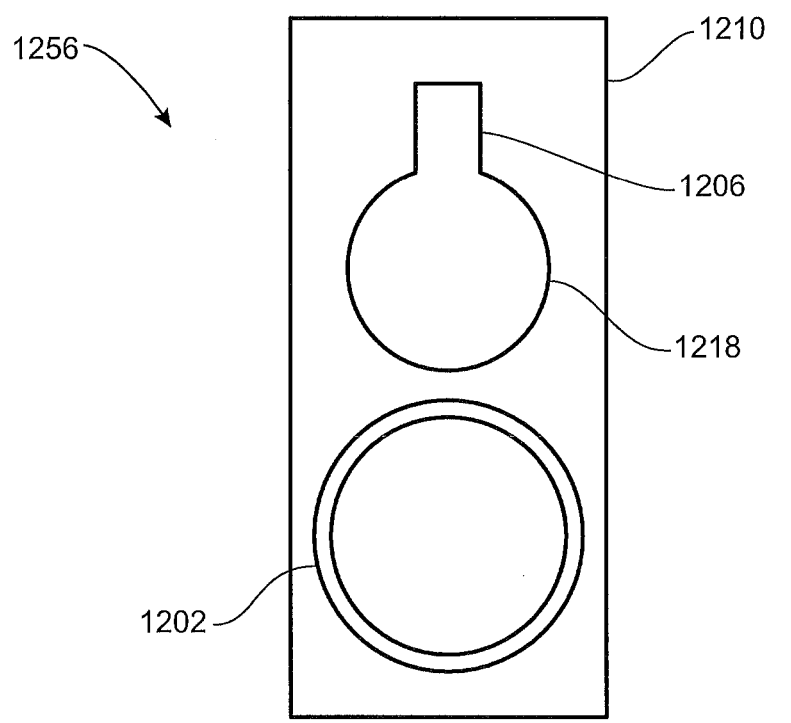
FIG. 12 is a cross-sectional view of another example of a vacuum pulsing device with a movable member thereof in a retracted position.
Figure 13:
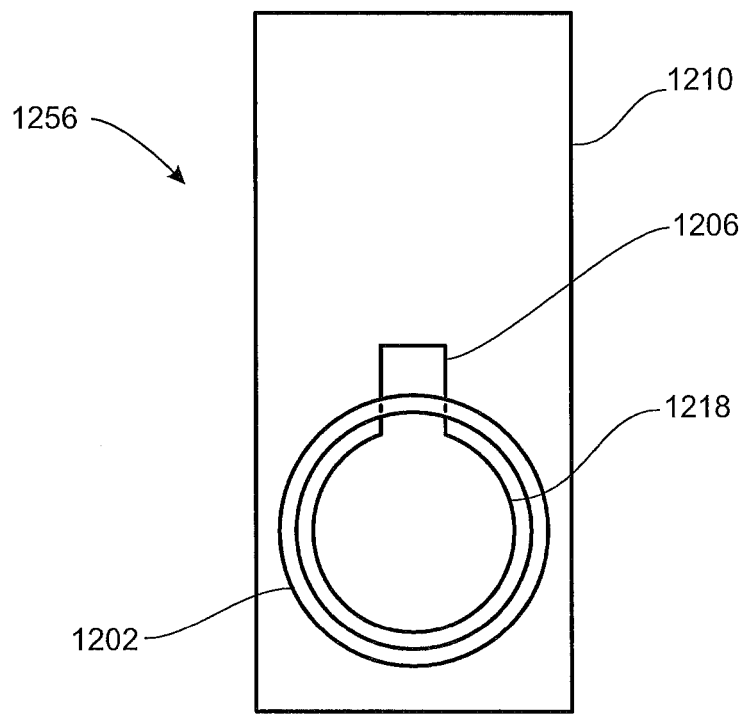
FIG. 13 is a cross-sectional view of the vacuum pulsing device illustrated in FIG. 12, with the movable member in its extended position.

FIGS. 12 and 13 are cross-sectional views of another example of a solenoid-based vacuum pulsing device 1256. The vacuum pulsing device 1256 includes a solenoid actuator 1210 and a movable member 1206 reciprocated by the actuator 1210 into and out from the flow path of an aspiration tube 1202 of the tissue removal device 104. FIG. 12 illustrates the movable member 1206 in its retracted position and FIG. 13 illustrates the movable member 1206 in its extended position. In this example, the movable member 1206 includes a distal section 1218 having a cross-sectional area substantially equal to the cross-sectional area of the aspiration tube 1202. By this configuration, the vacuum pulsing device 1256 effects complete or nearly complete occlusion of the flow path through the aspiration tube 1202 when the movable member 1206 is in the fully extended position.

Figure 14:
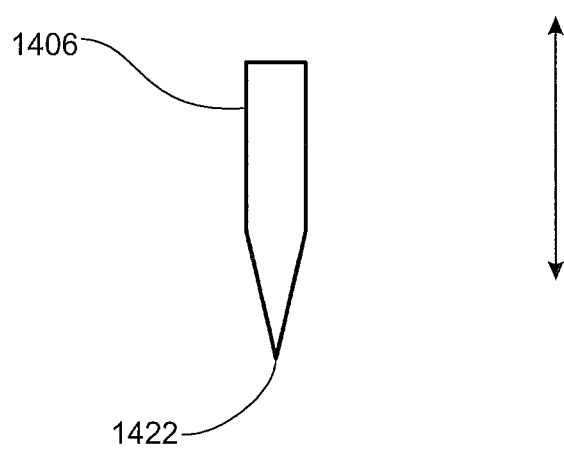
FIG. 14 is a side elevation view of an example of a movable member that may be provided in a vacuum pulsing device.

FIG. 14 is a side elevation view of a movable member 1406 from a perspective transverse to the direction of fluid flow in an aspiration tube. The movable member 1406 may be provided in a solenoid-based vacuum pulsing device such as described above in conjunction with FIGS. 10 and 11 or FIGS. 12 and 13. In this example, the movable member 1406 tapers down to a sharp edge 1422. By this configuration, the movable member 1406 may be utilized to further break up any tissue flowing through the aspiration tube while the movable member 1406 is being cycled into the aspiration tube.

Figure 15:
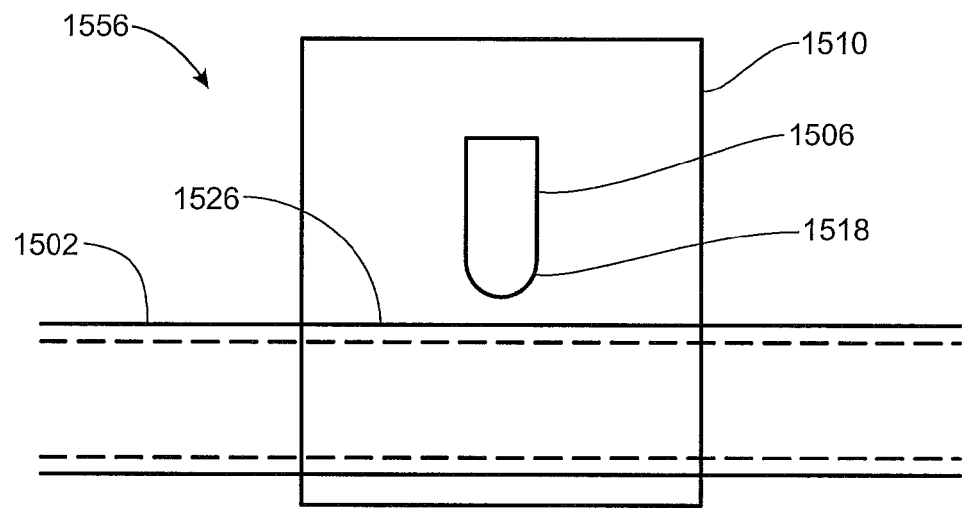
FIG. 15 is a cross-sectional view of another example of a vacuum pulsing device with a movable member thereof in a retracted position.
Figure 16:
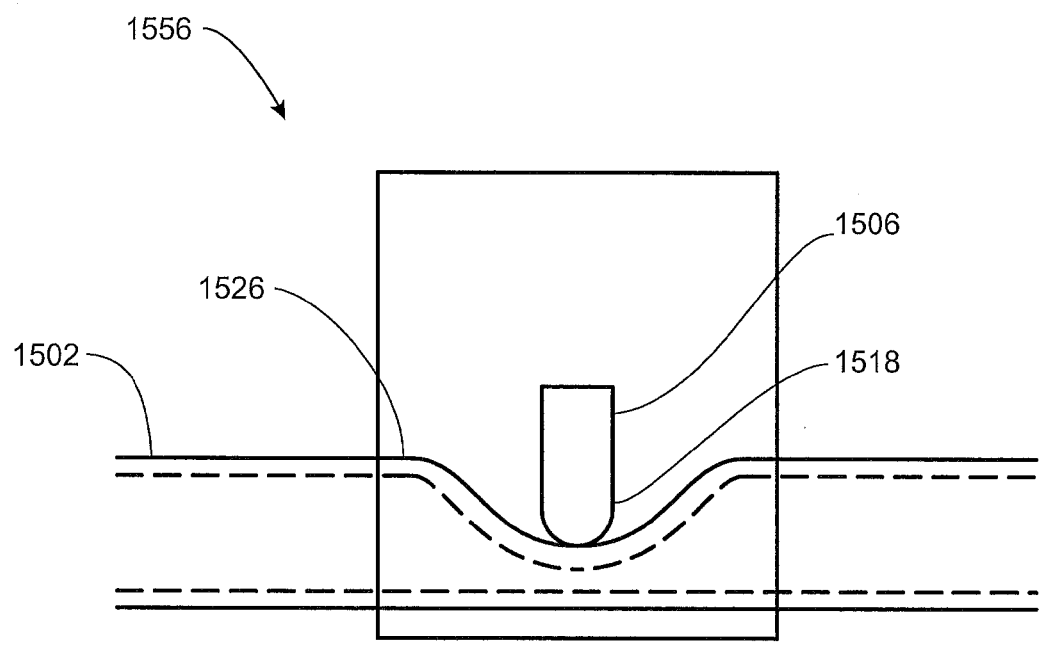
FIG. 16 is a cross-sectional view of the vacuum pulsing device illustrated in FIG. 14, with the movable member in its extended position.

FIGS. 15 and 16 are cross-sectional views of another example of a solenoid-based vacuum pulsing device 1556. The vacuum pulsing device 1556 includes a solenoid actuator 1510 and a movable member 1506 reciprocated by the actuator 1510 toward and away from the flow path of an aspiration tube 1502 of the tissue removal device 104. FIG. 15 illustrates the movable member 1506 in its retracted position and FIG. 16 illustrates the movable member 1506 in its extended position. In this example, the vacuum pulsing device 1556 is designed as a pinch valve. The movable member 1506 includes a distal section 1518 having a rounded end. A section 1526 of the aspiration tube 1502 immediately underneath the movable member 1506 is constructed from a deformable material (e.g., flexible tubing). As the movable member 1506 is translated to its fully extended position, the movable member 1506 comes into contact with the outside surface of the flexible section 1526 and deforms the flexible section 1526 until opposing regions of the inner wall of the flexible section 1526 come into contact with each other, thereby pinching off the flow path through the aspiration tube 1502.

Referring back to FIG. 1, the vacuum pump 108 generally includes a housing, a fluid inlet, a fluid outlet, and vacuum-generating components (not shown). The fluid inlet may be placed in fluid communication with the tissue removal device 104 via the (first) external aspiration line 152. The fluid outlet may be placed in fluid communication with the tissue collection site 128 via the outlet line 130. The external aspiration lines 152, 130, 164, 172 may have any suitable fluid-conducting structure (e.g., tubing), may be of any suitable length, and may be either rigid or flexible. The vacuum pump 108 may be any suitable pump for generating a controlled level of vacuum at the distal end 132 of the tissue removal device 104. The magnitude (or level) of vacuum may be set high enough to enable target tissue 120 to be aspirated through the cannula 148, the internal aspiration line 144, the first external aspiration line 152, the vacuum pump 108, the outlet line 130, and to the tissue collection site 128.

In some implementations, the vacuum pump 108 has a dual-cylinder configuration in which a pair of motorized syringe-type pumping units is disposed in the housing. In this case, the vacuum generating components may include a pair of cylinders, a pair of pistons reciprocating in the respective cylinders, and a pair of motors controlling the reciprocal movement of the respective pistons. The internal passages of the vacuum pump 108 may include a pair of inlet passages interconnecting the first aspiration line 152 and the respective cylinders, and a pair of outlet passages interconnecting the respective cylinders and the outlet line 130. Actively controlled valves may be provided in each inlet passage and outlet passage. The pistons are reciprocated at or about 180 degrees out-of-phase with each other. Accordingly, while one piston is executing a suction stroke the other piston is executing a discharge stroke. Consequently, while fluid from the first aspiration line 152 is being drawn into one cylinder, fluid previously drawn into the other cylinder is being discharged into the outlet line 130. In addition, a pair of pressure transducers may be disposed in fluid communication with the respective cylinders to measure the vacuum in each cylinder. An example of this type of dual-cylinder pump is described in U.S. Patent Application Pub. No. 2005/0234394, which is incorporated by reference herein in its entirety.

Continuing with this example, the motors of the vacuum pump 108 are in signal communication with the control console 112 via a motor control signal line 190. The valves are in signal communication with the control console 112 via a valve control signal line 192. The pressure transducers are in signal communication with the control console 112 via a pressure feedback signal line 194. By this configuration, the control console 112 is able to monitor and adjust the respective speeds of the pistons and their relative positions (i.e., relative timing or phasing), switch the positions of the valves between ON and OFF positions and possibly intermediate positions between the ON and OFF positions, and monitor the vacuum levels in each cylinder so as to make control decisions based on measured vacuum levels. By this configuration, the control console 112 is able to synchronize the respective operations of the motors and valves to maintain a constant vacuum level in the aspiration line 152. The vacuum level may be selected by the surgeon by manipulating controls on the control console 112 or the foot control device 116. This configuration also enables the vacuum pump 108 to respond quickly to real-time adjustments to the vacuum level made by the surgeon while minimizing transitory instabilities in the vacuum level caused by changing the vacuum level.

As diagrammatically illustrated in FIG. 1, the control console 112 may include a display 114 for outputting information to the surgeon. The control console 112 may also include a variety of controls or input mechanisms 118 (switches, knobs, keypad, etc.) for enabling the surgeon to input information, set and adjust various operating parameters of the tissue removal system 100 (e.g., vacuum pump(s) 108 and 168, vacuum pulsing device 156, thermal element 176, etc.), and program or adjust the control mechanisms provided by the foot control device 116. The control console 112 also includes electronic hardware (circuitry) and memory for storing software. The circuitry includes interface circuitry for enabling the respective operations of the display 114 and the input mechanisms 118, and for interfacing with the foot control device 116. The circuitry and software are configured for supporting the various functions of the tissue removal system 100. As examples, the circuitry may be configured for monitoring the operations of the vacuum pump(s) 108 and 168, the vacuum pulsing device 156, and the thermal element 176 and sending appropriate control signals to these components. Software may be provided for programming the circuitry for controlling these components in a manner appropriate for the particular tissue removal procedure to be performed. In some implementations, one or both vacuum pump(s) 108 and 168 may be mounted at or within the control console 112. In other implementations, one or both vacuum pump(s) 108 and 168 may be mounted at or within the foot control device 116.

By utilizing the input mechanisms of the control console 112 the surgeon may, as examples, switch the vacuum pump(s) 108 and 168 ON or OFF, set and vary the vacuum level generated by the vacuum pump(s) 108 and 168, switch the vacuum pulsing device 156 ON or OFF, set and vary the pulse frequency of the vacuum pulsing device 156 (thereby also controlling the flow rate of aspirated tissue), set and vary the magnitude of the vacuum pulses, switch the thermal element 176 ON or OFF, set and vary the amount of current fed to (and thereby control the operating temperature of) the thermal element 176, switch the thermal element 176 between a continuous heating mode and a pulsed heating mode, set and vary the frequency and magnitude of pulses of applied heat energy, etc. The control console 112 may also be configured to enable the surgeon to switch between a mode in which the surgeon can control the vacuum pulse rate and vacuum pulse magnitude (or the thermal pulse rate and thermal pulse magnitude) together as a single operating parameter by making a single adjustment, and a mode in which the surgeon can control the vacuum pulses rate and vacuum pulse magnitude (or the thermal pulse rate and thermal pulse magnitude) independently by manipulating two separate input mechanisms. Similarly, the control console 112 may be configured to enable the surgeon to switch between a mode in which the surgeon can control one or more operating parameters of the thermal element 176 together with one or more parameters of the vacuum pulsing device 156, and a mode in which the surgeon can control the operating parameters of the thermal element 176 independently of the operating parameters of the vacuum pulsing device 156.

The control console 112 may also be configured to enable the surgeon to switch the vacuum pulsing device 156 to a single-pulse mode that activates the vacuum pulsing device 156 only momentarily so as to apply a single pulse at a predetermined vacuum pulse magnitude. The single-pulse mode may be useful, for example, in an ophthalmological procedure that calls for creating an entry into the anterior capsule of a patient's eye. In this example, prior to breaking up target tissue, the distal tip of the cannula 148 may be placed into contact with the exterior of the anterior capsule. During this time, the tissue removal device 104 may be operated in the continuous-vacuum mode to assist in bringing the distal tip into contact with anterior capsule. The vacuum pulsing device 156 is then switched to the single-pulse mode, whereby the impact imparted by the single pulse is sufficient to create an entry into the anterior capsule through the thickness of its exterior structure. The distal tip is then inserted through the entry, at which time a tissue removal procedure may be performed. This technique enables the creation of an entry having a size and shape precisely conforming to the size and shape of the cannula 148, thereby providing a superior seal between the anterior capsule and the cannula 148.

The foot control device 116 may be configured for controlling one or more of the same functions controllable by the control console 112, such as those just described. Accordingly, the foot control device 116 may include one or more input mechanisms such as adjustable knobs 122 and depressible foot pedals 126. The foot pedals 126 may include foot switches and/or pivoting foot pedals. Foot switches may be operated to switch components of the tissue removal system 100 between ON and OFF states, or for clicking through incremental adjustments to operating parameters (e.g., selecting a high, medium or low setting for the applied vacuum or electrical energy). Pivoting foot pedals may be utilized to vary operating parameters between minimum and maximum values. The adjustable knobs 122 on the foot control device 116 or those on the control console 112 may be configured to enable the surgeon to set the minimum and maximum values of the pivoting foot pedal, and/or the rate (e.g., linear or exponential) by which an operating parameter changes in response to the pivoting travel of the foot pedal. As an example, pivoting the foot pedal forward from its base position to its halfway position may cause the associated operating parameter to be adjusted to a value that is exactly 50% of the preset maximum value. As another example, pivoting the foot pedal forward from its base position to its halfway position may result in adjusting the associated operating parameter to a value that is 75% of its preset maximum value, in which case adjusting the operating parameter over the other 25% up to the maximum value would require pivoting the foot pedal forward from the halfway position through the remaining portion of the pedal's travel. The control console 112 and/or the foot control device 116 may be configured to enable the surgeon to select which functions or operations are to be controlled by the control console 112 and which functions or operations are to be controlled by the foot control device 116. For simplicity, the foot control device 116 is diagrammatically illustrated in FIG. 1 as communicating with the control console 112 over a wired or wireless communication link 196. It will be understood, however, that depending on the functions controllable by the foot control device 116, various electrical signal lines may run directly to the foot control device 116 as an alternative or additionally to those communicating with the control console 112.

Figure 17:
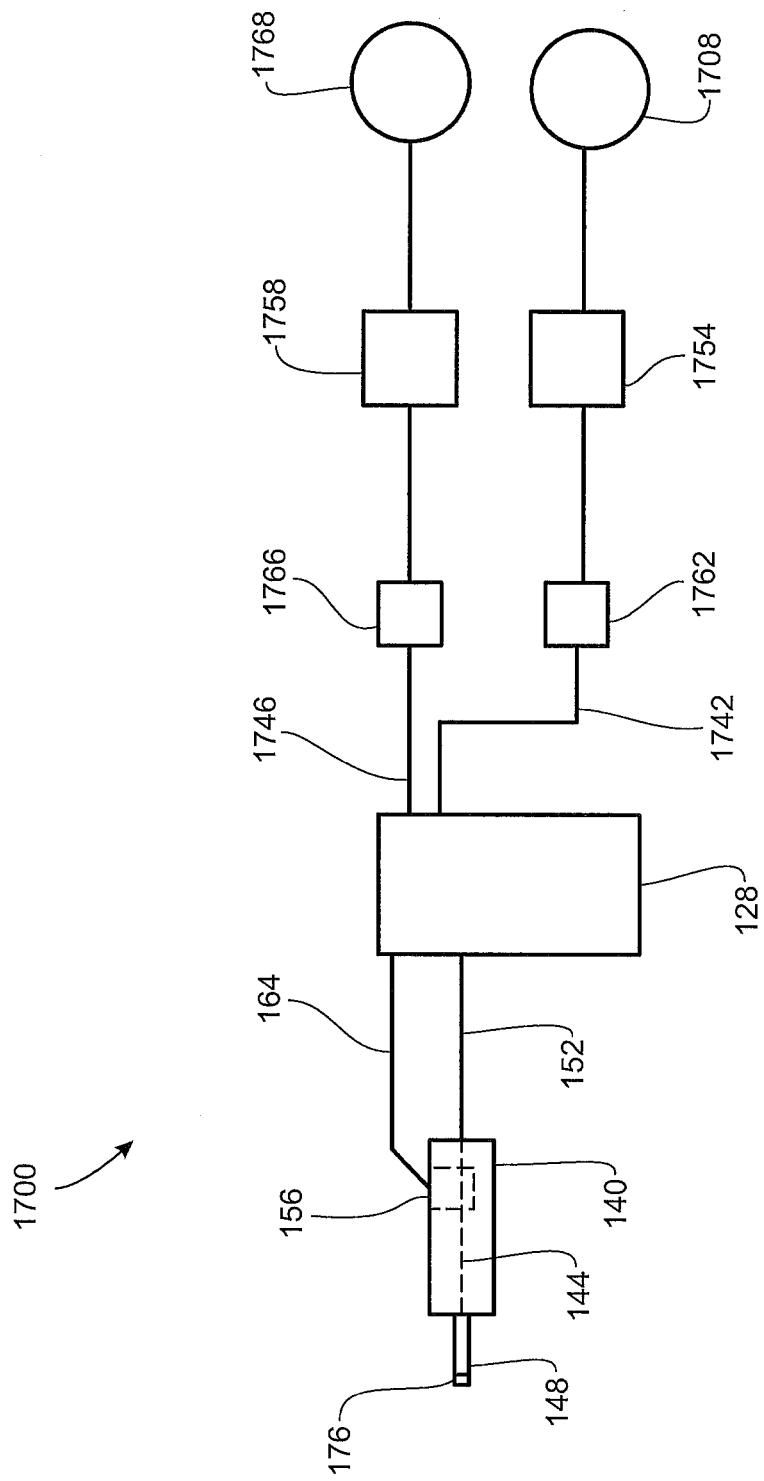
FIG. 17 is a block diagram illustrating an example of a tissue removal system according to another implementation.

FIG. 17 is a block diagram illustrating an example of a tissue removal system 1700 according to another implementation. For simplicity, the control console 112 and foot control device 116 (FIG. 1) are not illustrated in FIG. 17. The tissue removal system includes a first vacuum pump 1708 providing adjustable vacuum on the first aspiration line 152 during the continuous vacuum mode, and a second vacuum pump 1768 providing adjustable vacuum at relatively higher levels on the second aspiration line 164 during the pulsed vacuum mode. As noted previously, the vacuum pulsing device 156 or other component of the tissue removal device 104 may be configured for switching the aspiration path from the cannula 148 between the first aspiration line 152 and the second aspiration line 164 in accordance with vacuum mode selected. In this example, the vacuum pumps 1708, 1768 are configured as gas (e.g., air) pumps instead of the liquid pumps described earlier in this disclosure. The tissue collection device 128 is interconnected between the tissue removal device 104 and the vacuum pumps 1708, 1768 via the aspiration lines 152, 164 and respective outlet lines 1742, 1746. The tissue collection device 128 may be configured in a conventional manner for removing aspirated fluid and tissue such that only gas is routed through the outlet lines 1742, 1746. Alternatively, separate tissue collection devices may be provided for the two aspiration lines 152, 164. Typically, vacuum reservoirs 1754, 1758 are provided upstream of the respective vacuum pumps 1708, 1768 to assist in building vacuum. Alternatively, both vacuum pumps 1708, 1768 may communicate with a single vacuum reservoir. One or more pressure regulators 1762, 1766 of any suitable design may be provided in fluid communication with the respective vacuum pumps 1708, 1768 as needed. The pressure regulators 1762, 1766 may be of the type that can be controlled by the control console 112 or the foot control device 116. One or more of the foregoing components (vacuum pumps 1708, 1768, vacuum reservoirs 1754, 1758, pressure regulators 1762, 1766, tissue collection device 128) may be mounted at or within the control console 112 or the foot control device 116. The tissue removal system 1700 illustrated in FIG. 17 may operate in a manner similar to that described above for the tissue removal system 100 illustrated in FIG. 1.

Figure 18:
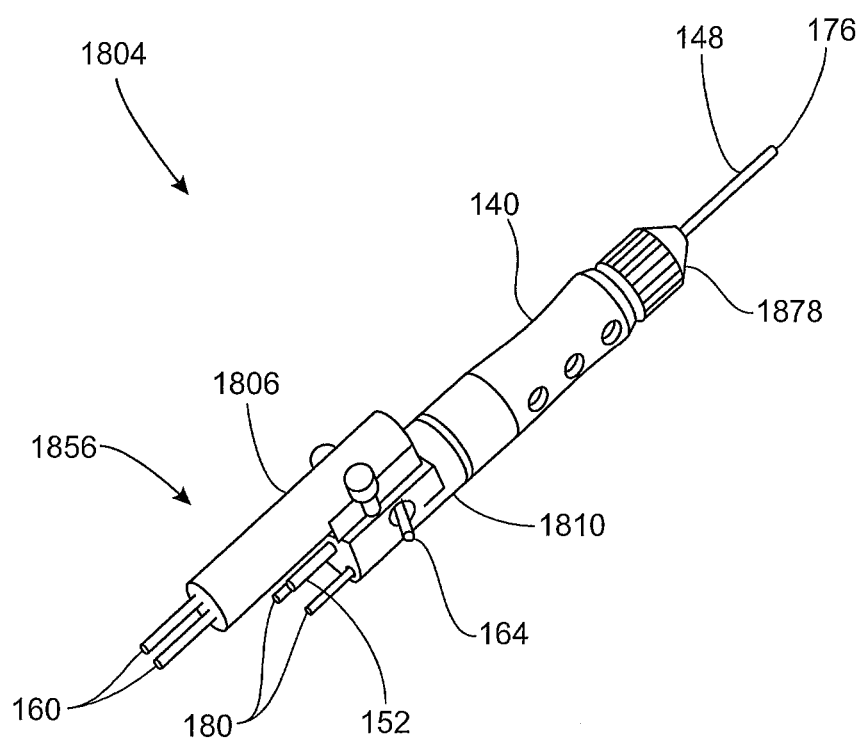
FIG. 18 is a perspective view of an example of a tissue removal device according to another implementation.
Figure 19:
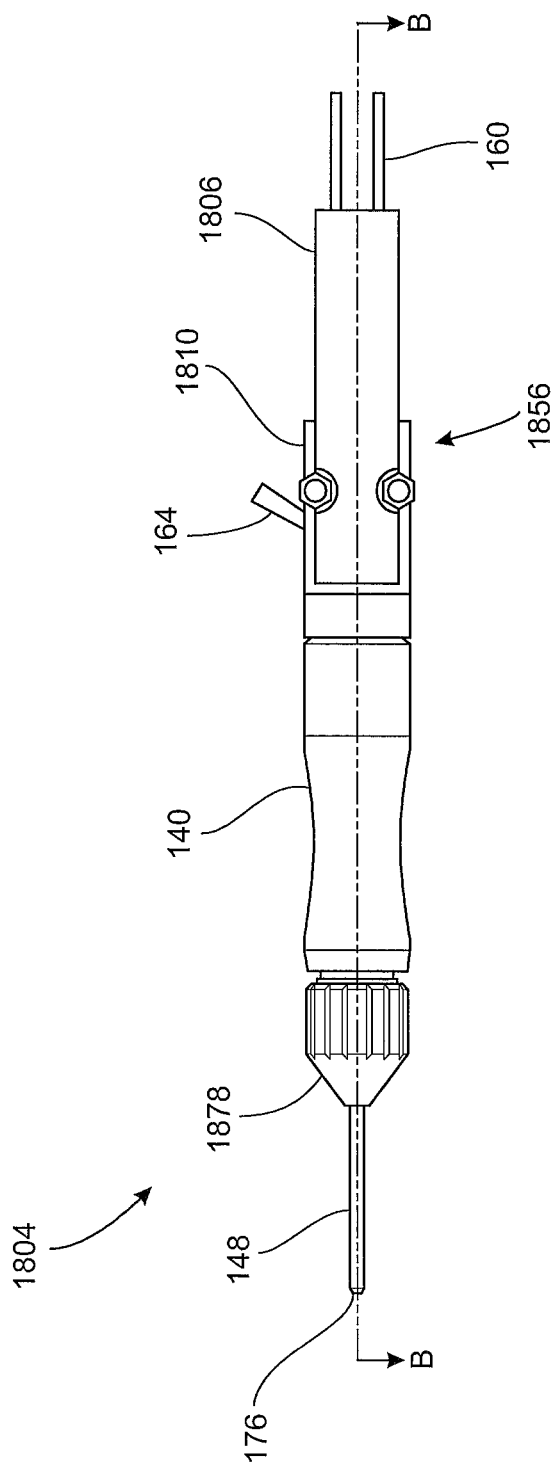
FIG. 19 is a top plan view of the tissue removal device illustrated in FIG. 18.
Figure 20:
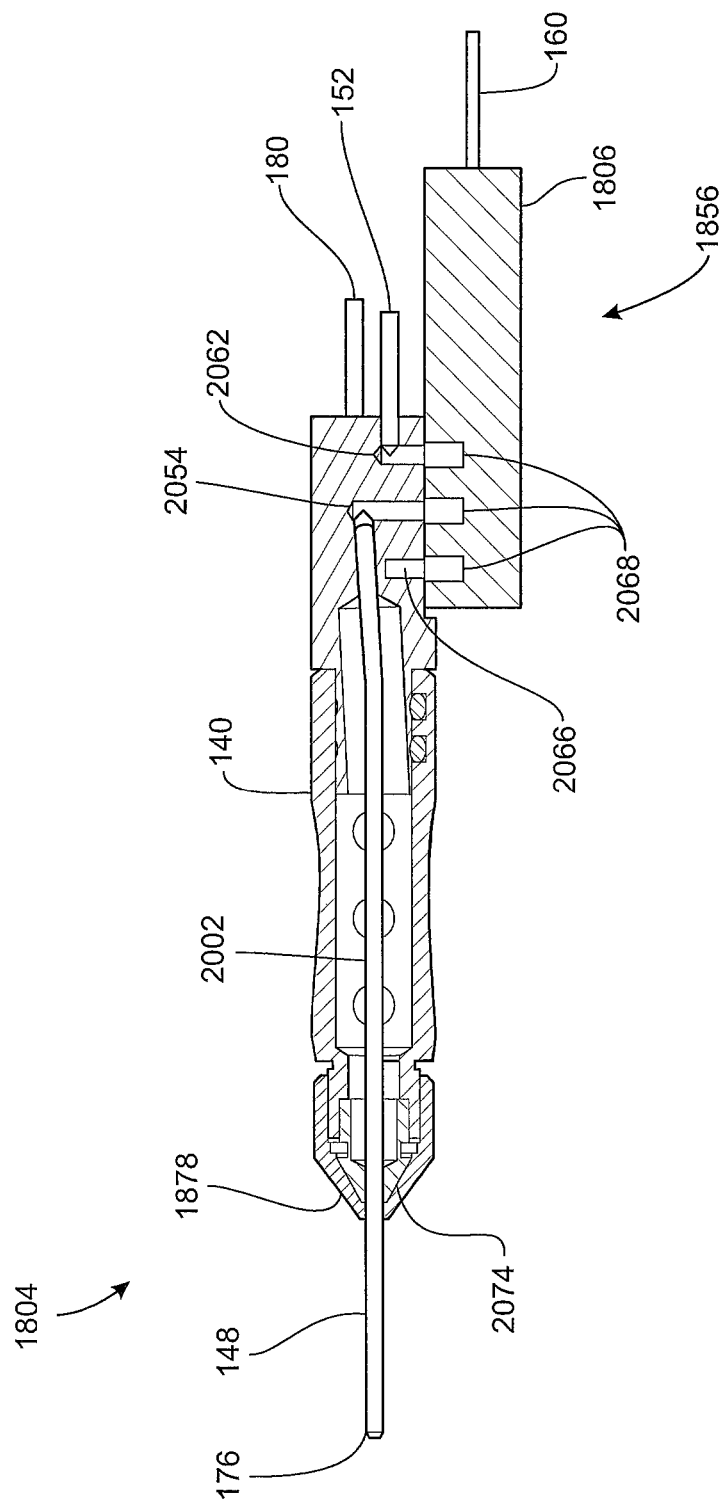
FIG. 20 is a cross-sectional view of the tissue removal device taken along line B-B of FIG. 19.

FIGS. 18, 19 and 20 illustrate an example of a tissue removal device 1804 according to another implementation. Specifically, FIG. 18 is a perspective view of the tissue removal device 1804, FIG. 19 is a top plan view of the tissue removal device 1804, and FIG. 20 is a cross-sectional view of the tissue removal device 1804 taken along line B-B of FIG. 19. In this example and as described earlier, the tissue removal device 1804 is configured for operation with two aspiration lines 152, 164 extending from proximal openings of the housing 140, in which one aspiration line 152 is utilized during the continuous vacuum mode and the other aspiration line 164 is utilized during the pulsed vacuum mode. Alternatively, the tissue removal device 1804 may be configured for operation with only a single aspiration line. In this example, the cannula 148 is connected to an internal aspiration tube 2002 within the housing 140. The cannula 148 may have the split design described earlier in this disclosure, with structural halves of the cannula 148 connected to respective insulated wires that run through the housing 140 to respective outbound wires serving as the heating signal line 180. The cannula 148 may extend outward from a distal opening of the housing 140 formed by an internal hub 2074 and a coaxial, threaded locking mechanism 1878 to enable quick assembly and disassembly of the tissue removal device 1804.

Also in the example illustrated in FIGS. 18, 19 and 20, the tissue removal device 1804 includes a solenoid-based vacuum pulsing device 1856. The vacuum pulsing device 1856 includes a solenoid block 1810 attached to the proximal end of the housing 140 and a solenoid actuator 1806. The solenoid block 1810 includes a common port 2054 in fluid communication with the internal aspiration tube 2002, a low-vacuum port 2062 in fluid communication with the first aspiration line 152, and a high-vacuum port 2066 in fluid communication with the second aspiration line 164. The actuator 1806 may be provided in the form of a spool valve, the general operation of which is known to persons skilled in the art. In this case, the movable member that is actuated by the actuator 1806 is a spool that translates back and forth relative to the solenoid block 1810. The position of the spool determines whether the common port 2054 is in fluid communication with either the low-vacuum port 2062 or the high-vacuum port 2066, by means of interconnecting passages or channels 2068 that are active or inactive depending on the spool position. The spool is thus utilized to switch the tissue removal device 1804 between the continuous vacuum mode and the pulsed vacuum mode. In the continuous vacuum mode, the common port 2054 is in fluid communication with the low-vacuum port 2062 and aspirated material is routed from the cannula 148 to the first aspiration line 152 under the influence of the first vacuum pump. In the pulsed vacuum mode, the common port 2054 is in fluid communication with the high-vacuum port 2066 and aspirated material is routed from the cannula 148 to the second aspiration line 164 under the influence of the second vacuum pump. In this example, the vacuum pulsing device 1856 may be configured to generate vacuum pulses by rapidly translating the spool back and forth so as to alternately open and close the fluid path between the common port 2054 and the high-vacuum port 2066.

Figure 21:
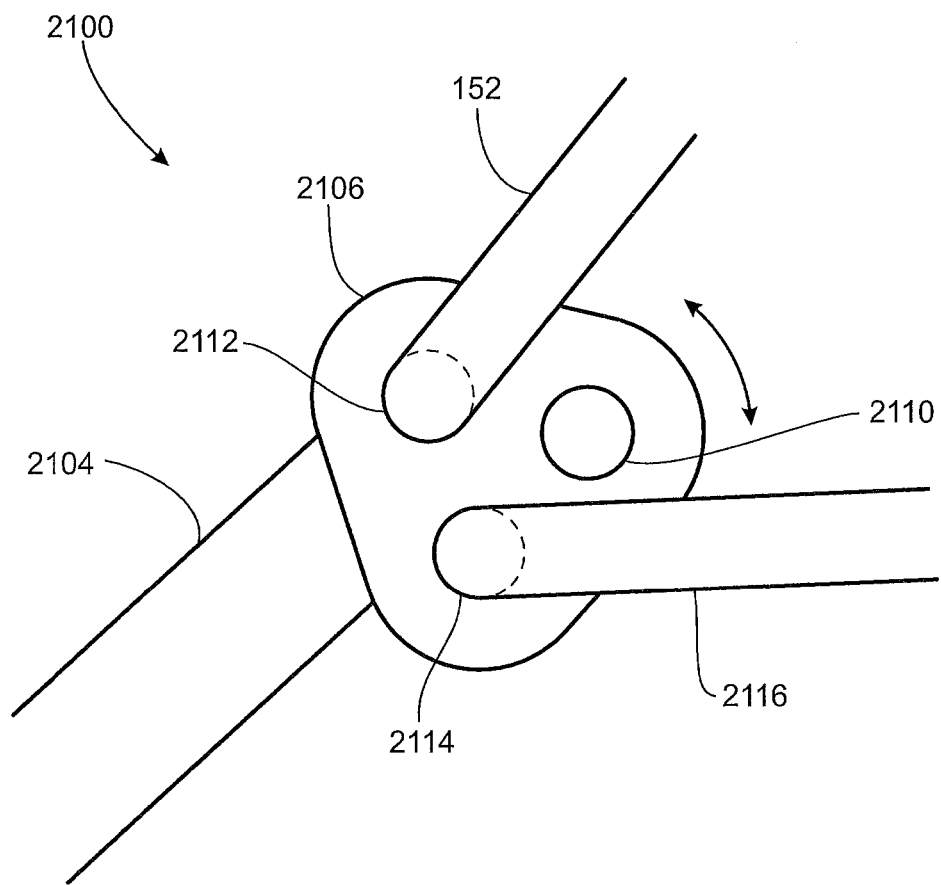
FIG. 21 is a perspective view of an example of a hand-held surgical instrument according to another implementation.

FIG. 21 is a perspective view of example of a hand-held surgical instrument 2100 according to another implementation. The surgical instrument 2100 is configured as a multi-function instrument in which one or more functions in addition to tissue aspiration may be selected by the surgeon. For this purpose, the surgical instrument 2100 includes a rotatable hub 2106 located at its proximal end. The rotatable hub 2106 may be rotated by the surgeon about a pivot 2110 supported by the surgical instrument 2100. The rotatable hub 2106 includes a vacuum port or bore 2112 connectable to vacuum tubing 152 and one or more additional ports or bores 2114 connectable to corresponding additional tubing 2116. The additional ports 2114 may be utilized as injection bores for adding specific types of materials to the surgical site as noted previously in this disclosure, by flowing such materials through the surgical instrument 2100 and the same cannula utilized for tissue aspiration. The interface between the rotatable hub 2106 and the surgical instrument 2100 is configured such that incremental rotation locks a desired port 2112 or 2114 into fluid communication with the internal passages of the surgical instrument 2100 normally employed for vacuum application and fluid and tissue flow. In one implementation, the additional port 2114 and tubing 2116 are utilized for injecting liquid IOL material as part of an endocapsular procedure. After the vacuum port 2112 has been employed to remove a cataract, the surgeon rotates the hub 2106 to switch in the additional port 2114 that is connected to a source of IOL material. The surgeon then utilizes the surgical instrument 2100 to inject the liquid IOL material into the capsular bag of the eye via the tubing 2116 that serves as the IOL material supply line. This configuration avoids requiring the surgeon to remove the vacuum cannula from the eye and subsequently insert—through the previously created, small anterior capsule incision—another separate cannula for the purpose of injecting the liquid IOL material. This is advantageous because in order to perform the endocapsular procedure, the incision made in the anterior capsule must perfectly match the cannula being utilized. Any movement of the cannula might tear or damage the incision, which would compromise the incision and make it more difficult to seal the incision to prevent the liquid IOL material from leaking out from the capsular bag.

Figure 22:
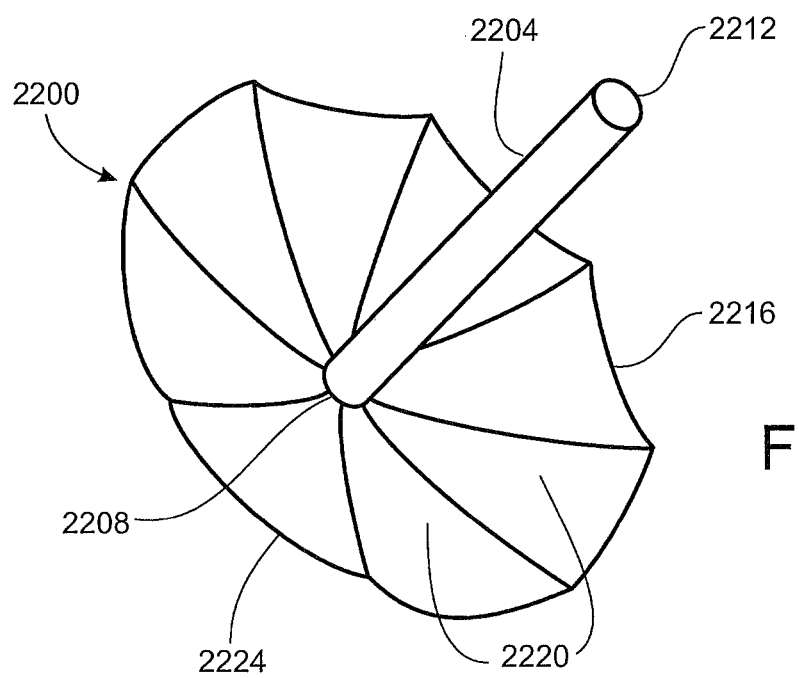
FIG. 22 is a perspective view of an example of an expandable incision seal according to an implementation disclosed herein, with the seal in an expanded position.
Figure 23:
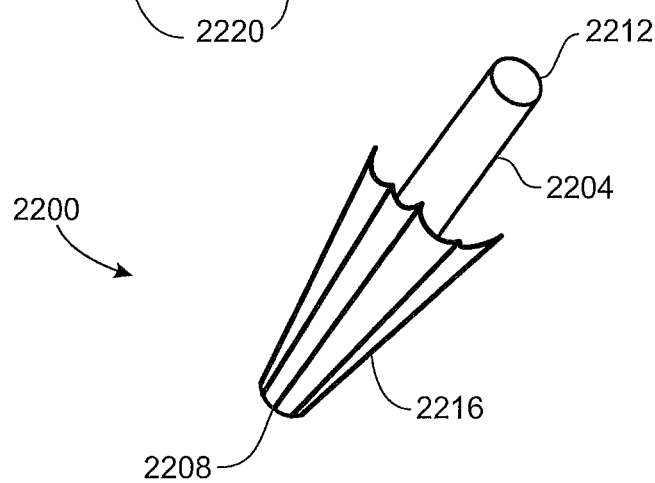
FIG. 23 is a perspective view of the expandable seal illustrated in FIG. 22, with the seal in a retracted position.

FIGS. 22 and 23 are perspective views of an example of an expandable incision seal 2200 that may be utilized to seal an incision made during an endocapsular procedure or other type of procedure. FIG. 22 shows the incision seal 2200 in an expanded position, while FIG. 23 shows the incision seal 2200 in a retracted position. The incision seal 2200 includes a shaft 2204 sized to fit into and completely fill the opening defined by an incision. The shaft 2204 includes a distal end 2208 and a proximal end 2212. The incision seal 2200 also includes an expandable portion 2216 adjoining the distal end 2208. The expandable portion 2216 is configured in the manner of an umbrella. Accordingly, the expandable portion 2216 includes a plurality of radial segments or panels 2220 extending outward in radial directions from the distal end 2208, with adjacent segments 2220 being adjoined at radial fold lines 2224. The expandable portion 2216 is movable from the retracted position shown in FIG. 23 at which the segments 2220 are oriented at a first angle relative to the shaft 2204, to the expanded position shown in FIG. 22 at which the segments 2220 are disposed at a second angle relative to the shaft 2204 greater than the first angle. In addition to functioning as a seal, the incision seal 2200 may be utilized as a plunger to push viscous materials through a tissue removal device or other surgical instrument (e.g., the surgical instrument 2100 shown in FIG. 21) and into the surgical site.

In the example of an IOL procedure, the incision seal 2200 may initially be lightly (or loosely, etc.) attached at its proximal end 2212 to an elongated rod or wire of a separate instrument. The proximal end 2212 may be configured by any suitable means to effect this attachment. With the surgical instrument 2100 set such that the IOL material line 2116 (FIG. 21) fluidly communicates with the cannula of the surgical instrument 2100, the surgeon injects the IOL material into the IOL material line 2116. With the shaft 2204 of the incision seal 2200 attached to the rod of the separate instrument, the surgeon may then insert the incision seal 2200 into the IOL material line 2116 and push the incision seal 2200 therethrough by pushing the rod of the separate instrument. The incision seal 2200 easily travels through the IOL material line 2116 in the retracted position shown in FIG. 23. The IOL material may be highly viscous and require assistance in being inserted through the incision into the capsular bag. Accordingly, the distal end 2208 may be utilized to push the IOL material through the IOL material line 2116. The surgeon may push the incision seal 2200 through the cannula of the surgical instrument 2100 and into the incision. The surgeon may push the incision seal 2200 far enough through the incision that the expandable portion 2216 clears the incision and is disposed completely in the capsular bag. At this time, the shaft 2204 of the incision seal 2200 extends through the incision and the tissue boundary defining the incision fits tightly around the shaft 2204. The surgeon may then pull on the rod of the separate instrument whereby the shaft 2204 begins to retract out from the incision. This pulling causes the expandable portion 2216 of the incision seal 2200 to expand outwardly to the expanded position shown in FIG. 22. In the expanded position, the expandable portion 2216 abuts against the posterior surface of the anterior capsule in the vicinity surrounding the incision. The shaft 2204 and the expandable portion 2216 thus form a fluid-tight seal in and around the incision. Moreover, because the expandable portion 2216 is now in its expanded position and is located on the inner side of the incision, the expandable portion 2216 cannot be removed from the anterior capsule and consequently the shaft 2204 cannot be completely retracted from the incision because the expandable portion 2216 remains anchored to the shaft 2204. However, as noted above the rod of the separate instrument is merely lightly attached to the shaft 2204. Hence, when the surgeon pulls back on the rod, the rod is detached from the shaft 2204 and then may be easily removed from the surgical site via retraction through the cannula of the surgical instrument 2100 after the incision seal 2200 has been properly installed in the incision in the manner just described.

The expandable incision seal 2200 may be constructed from any materials suitable for enabling the functions and operations described above in conjunction with FIGS. 22 and 23.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A tissue removal device, comprising:
a handpiece enclosing a handpiece interior and having a proximal handpiece opening and a distal handpiece opening;
a vacuum conduit extending from the proximal handpiece opening and through the handpiece interior and the distal handpiece opening, and terminating at an open distal conduit end disposed outside the handpiece at a distance from the distal handpiece opening, the vacuum conduit including a rigid conduit section extending along at least a portion of the vacuum conduit to the distal conduit end, wherein the vacuum conduit defines a fluid path;
a valve mechanism comprising an actuator and a movable member movable by the actuator in the rigid conduit section to alternately open and close the fluid path, wherein the valve mechanism generates vacuum pulses at a pulse rate and pulse magnitude effective for breaking up target tissue; and
a vacuum control device communicating with the valve mechanism and comprising pulse rate control circuitry configured to control a pulse rate of the vacuum pulses, and vacuum-mode switching circuitry configured to switch the valve mechanism between a continuous-vacuum mode and a pulsed vacuum mode,
wherein, in the continuous-vacuum mode the vacuum control device is configured to provide a base vacuum magnitude, and in the pulsed vacuum mode the vacuum control device is configured to provide the pulse magnitude at a level higher than the base vacuum magnitude.

2. The tissue removal device of claim 1, wherein the pulse rate control circuitry includes a pulse rate controller disposed remotely from the handpiece and selected from the group consisting of a user-operated console input and a user-operated foot switch.

3. The tissue removal device of claim 1, wherein the vacuum-mode switching circuitry includes a switch disposed remotely from the handpiece and selected from the group consisting of a user-operated console switch and a user-operated foot switch.

4. The tissue removal device of claim 1, wherein the vacuum-mode switching circuitry is configured to switch the valve mechanism between a single-pulse vacuum mode and a pulse-train vacuum mode.

5. The tissue removal device of claim 4, wherein the vacuum-mode switching circuitry includes a switch disposed remotely from the handpiece and selected from the group consisting of a user-operated console switch and a user-operated foot switch.

6. The tissue removal device of claim 1, wherein at least a portion of the valve mechanism is enclosed in the handpiece.

7. The tissue removal device of claim 1, further including a vacuum transducer configured to measure a vacuum level in the vacuum conduit and communicating with the vacuum control circuitry, wherein the vacuum control circuitry is configured to switch the valve mechanism between a plurality of different vacuum control modes in response to a vacuum-level measurement signal received from the vacuum transducer.

8. The tissue removal device of claim 1, wherein the vacuum control device is configured to control a level of vacuum in the vacuum conduit and configured to be switched between a first control mode in which vacuum level and pulse rate are adjusted together and a second control mode in which vacuum level and pulse rate are adjusted independently.

9. The tissue removal device of claim 1, wherein the movable member comprises a plunger movable through the vacuum conduit, and further comprising a flexible sealing element attached to a distal plunger end of the plunger.

\* \* \* \* \*